US009523693B2

(12) United States Patent
Nordlund et al.

(10) Patent No.: US 9,523,693 B2
(45) Date of Patent: *Dec. 20, 2016

(54) METHODS FOR DETERMINING LIGAND BINDING TO A TARGET PROTEIN USING A THERMAL SHIFT ASSAY

(71) Applicant: Biotarget Engagement Interest Group AB, Solna (SE)

(72) Inventors: Pär Nordlund, Stockholm (SE); Daniel Martinez Molina, Stockholm (SE); Thomas Lundbäck, Solna (SE)

(73) Assignee: Biotarget Engagement Interest Group AB, Solna (SE)

( * ) Notice: Subject to any disclaimer, the term of this patent is extended or adjusted under 35 U.S.C. 154(b) by 29 days.

This patent is subject to a terminal disclaimer.

(21) Appl. No.: 14/599,256

(22) Filed: Jan. 16, 2015

(65) Prior Publication Data
US 2015/0133336 A1   May 14, 2015

Related U.S. Application Data

(63) Continuation-in-part of application No. 14/057,920, filed on Oct. 18, 2013, now Pat. No. 8,969,014, which is a continuation of application No. PCT/GB2012/050853, filed on Apr. 18, 2012.

(30) Foreign Application Priority Data

Apr. 18, 2011   (GB) .................................. 1106548.9

(51) Int. Cl.
G01N 33/68        (2006.01)
G01N 33/53        (2006.01)

(52) U.S. Cl.
CPC ...... *G01N 33/6845* (2013.01); *G01N 33/5306* (2013.01)

(58) Field of Classification Search
None
See application file for complete search history.

(56) References Cited

U.S. PATENT DOCUMENTS

| | | | |
|---|---|---|---|
| 6,036,920 | A | 3/2000 | Pantoliano et al. |
| 6,171,850 | B1 | 1/2001 | Nagle et al. |
| 8,969,014 | B2 | 3/2015 | Nordlund |
| 2002/0114734 | A1 | 8/2002 | Pantoliano et al. |
| 2005/0006372 | A1 | 1/2005 | Murakami et al. |
| 2010/0256342 | A1 | 10/2010 | Salemme et al. |
| 2011/0124120 | A1 | 5/2011 | Kranz et al. |
| 2015/0140575 | A1 | 5/2015 | Nordlund |

FOREIGN PATENT DOCUMENTS

| | | |
|---|---|---|
| EP | 1639373 B1 | 3/2006 |
| WO | 86/06492 A1 | 11/1986 |
| WO | 97/42500 A1 | 11/1997 |
| WO | 99/24050 A1 | 5/1999 |
| WO | 01/46693 A2 | 6/2001 |
| WO | 02/103321 A2 | 12/2002 |
| WO | 2004/101790 A1 | 11/2004 |
| WO | 2005/107938 A2 | 11/2005 |
| WO | 2006/110292 A2 | 10/2006 |
| WO | 2010/151180 A1 | 12/2010 |

OTHER PUBLICATIONS

Crowther (ELISA Guidebook 2002, excerpt p. 1-3, not including cover page).*
Cimmperman, Piotras et al., "A Quantitative Model of Thermal Stabilization and Destabilization of Proteins by Ligands," Biophysical Journal, vol. 95:3222-3231 (2008).
Ericsson, U.B. et al., "Thermofluor-based high-throughput stability optimization of proteins for structural studies," Analytical Biochemistry, vol. 357(2):289-298 (2006).
Kim, Jae-Young et al., "Temperature-Triggered Purification of Antibodies," Biotechnology and Bioengineering, vol. 90(3):373-379 (2005).
Knaust, R.K. et al., "Screening for soluble expression of recombinant proteins in a 96-well format," Analytical Biochemistry, vol. 297(1):79-85 (2001).
Lomenick, Brett et al., "Target identification using drug affinity responsive target stability (DARTS)," PNAS, vol. 106(51):21984-21989 (2009).
Minagawa, H. et al., "Improving the thermal stability of lactate oxidase by directed evolution," Cell. Mol. Life Sci., vol. 64:77-81 (2007).
Moreau, Morgane J.J. et al., "Quantitative determination of protein stability and ligand binding using a green fluorescent protein reporter system," Molecular Biosystems, vol. 6(7):1285-1292 (2010).

(Continued)

*Primary Examiner* — Jacob Cheu
(74) *Attorney, Agent, or Firm* — Nelson Mullins Riley & Scarborough LLP; Jane E. Remillard, Esq.; Jill Gorny Sloper, Esq.

(57) ABSTRACT

The present invention concerns a method of determining whether a non-purified sample contains a target protein bound to a ligand of interest comprising the steps of a) exposing the non-purified sample to a temperature which is capable of causing or enhancing precipitation of the unbound target protein to a greater extent than it is capable of causing or enhancing precipitation of the target protein bound to the ligand; and b) analyzing said sample for the presence of soluble or native target protein using two or more affinity reagents capable of binding to said soluble or native target protein with a higher affinity than to an unfolded and/or insoluble form of said target protein. The invention particularly concerns the use of two affinity reagents (e.g. antibodies) which are capable of distinguishing between soluble or native, and unfolded and/or insoluble forms of a target protein and whose detection e.g. by FRET based technology, allows the performance of the method without a separation step.

17 Claims, 18 Drawing Sheets

(56) References Cited

OTHER PUBLICATIONS

Pantoliano, Michael W. et al., "High-Density Miniaturized Thermal Shift Assays as a General Strategy for Drug Discovery," Journal of Biomolecular Screening, vol. 6(6):429-440 (2001).
Pohn, Brigitte et al., "Micro-colony array based high throughput platform for enzyme library screening," Journal of Biotechnology, vol. 129:162-170 (2007).
Reetz, Manfred T. et al., "Iterative saturation mutagenesis (ISM) for rapid directed evolution of functional enzymes," Nature Protocols, vol. 2(4):891-903 (2007).
Senisterra, Guillermo A. et al., "Application of High-Throughput Isothermal Denaturation to Assess Protein Stability and Screen for Ligands," Journal of Biomolecular Screening, vol. 13(5):337-342 (2008).
Song, Jae Kwang et al., "Enhancement of stability and activity of phospholipase A1 in organic solvents by directed evolution," Biochimica et Biophysica Acta, vol. 1547:370-378 (2001).
Vedadi, Masoud et al., "Chemical screening methods to identify ligands that promote protein stability, protein crystallization, and structure determination," PNAS, vol. 103(43):15835-15840 (2006).
West, Graham M. et al., "Mass Spectrometry-Based Thermal Shift Assay for Protein-Ligand Binding Analysis," Analytical Chemistry, vol. 62(13):5573-5581 (2010).
International Preliminary Report on Patentability for Application No. PCT/GB2012/050853, 4 pages, dated Jan. 22, 2013.
International Search Report and Written Opinion for Application No. PCT/GB2012/050853, 8 pages, dated Jun. 5, 2012.
Anderson, N. Leigh et al., "Analytical Techniques for Cell Fractions. XXIII. A Stable Thermal Gradient Device for Heat Denaturation Studies on Proteins," Analytical Biochemistry, vol. 91:441-445 (1978).
Anderson, N. Leigh et al., "The beta and gamma Cytoplasmic Actins are Differentially Thermostabilized by MgADP; gamma Actin Binds MgADP More Strongly," Biochemical and Biophysical Research Communications, vol. 89(2):486-490 (1979).
Almqvist, H. et al., "High Throughput Adaptation of the Cellular Thermal Shift Assay (CETSA) using AlphaScreen® Technology to Monitor Target Engagement in Cells," Poster Presentation, 2013, p. 1.
Bembenek, M. et al, "Determination of Complementary Antibody Pairs Using Protein A Capture with the AlphaScreen Assay Format," Analytical Biochemistry, 2011, vol. 408, pp. 321-327.
Jafari, et al., "The Cellular Thermal Shift Assay for Evaluating Drug Target Interactions in Cells," Nature Protocols, 2014, vol. 9, No. 9, pp. 2100-2123.
Molina, Daniel Martinez, et al., "Monitoring Drug Target Engagement in Cells and Tissues Using the Cellular Thermal Shift Assay," Science, 2013, vol. 341, pp. 84-87.
Perkin Elmer, "AlphaScreen® SureFire® p-ERK ½ (Thr202/Tyr204) Assay Kits Manual," Mar. 2, 2011, pp. 1-22.
Savitski et al., "Tracking Cancer Drugs in Living Cells by Thermal Profiling of the Proteome," Science, 2014, vol. 346, Issue 6205, pp. 1-10.
U.S. Appl. No. 14/602,993, Jun. 7, 2016.

\* cited by examiner

| 50 µM | 1 | 2 | 3 | 4 | 5 | 6 | 7 | 8 | 9 | 10 | 11 |
|---|---|---|---|---|---|---|---|---|---|---|---|
| A | 25354 | 33528 | 21507 | 22748 | 44164 | 31203 | 16391 | 20692 | 36351 | 20042 | 15393 |
| B | 22445 | 20057 | 12680 | 27454 | 20478 | 28085 | 14612 | 18705 | 15233 | 15910 | 12595 |
| C | 21333 | 22449 | 11923 | 19705 | 10858 | 9517 | 18642 | 14037 | 14393 | 15261 | 10241 |
| D | 29479 | 331959 | 16933 | 13745 | 11320 | 19635 | 19389 | 15969 | 16015 | 15814 | 14365 |
| E | 18796 | 17241 | 12648 | 11831 | 15782 | 82547 | 19302 | 15449 | 339624 | 22983 | 13368 |
| F | 17779 | 10771 | 12813 | 12582 | 11680 | 11009 | 16271 | 12071 | 9844 | 16573 | 17487 |
| G | 17027 | 11487 | 13260 | 11181 | 10952 | 9675 | 20113 | 86033 | 11295 | 13393 | 21701 |
| H | 11297 | 8682 | 17657 | 13435 | 12216 | 15171 | 16256 | 21713 | 17975 | 28894 | 38892 |

| 10 µM | 1 | 2 | 3 | 4 | 5 | 6 | 7 | 8 | 9 | 10 | 11 |
|---|---|---|---|---|---|---|---|---|---|---|---|
| A | 24458 | 38252 | 21292 | 60109 | 30179 | 40126 | 29747 | 31927 | 27031 | 14739 | 17327 |
| B | 9770 | 22069 | 17327 | 30755 | 29889 | 20990 | 20935 | 17026 | 13066 | 23363 | 19650 |
| C | 15082 | 14744 | 19437 | 28073 | 14932 | 16825 | 22375 | 19257 | 11407 | 19080 | 16390 |
| D | 13123 | 305405 | 19897 | 22773 | 16157 | 21918 | 15590 | 10305 | 16569 | 17172 | 18077 |
| E | 18041 | 18594 | 13604 | 23721 | 17486 | 25123 | 17108 | 13999 | 307527 | 8974 | 24451 |
| F | 15435 | 17069 | 21076 | 11981 | 12799 | 21702 | 12118 | 11848 | 10063 | 8057 | 13414 |
| G | 9383 | 12226 | 14248 | 11240 | 15654 | 18025 | 11446 | 24869 | 11213 | 14340 | 25430 |
| H | 10269 | 19680 | 19763 | 20073 | 12620 | 23826 | 16597 | 11066 | 14189 | 9243 | 25809 |

Figure 14A

METHODS FOR DETERMINING LIGAND BINDING TO A TARGET PROTEIN USING A THERMAL SHIFT ASSAY

CROSS-REFERENCE TO RELATED APPLICATIONS

This application is a continuation-in-part of U.S. patent application Ser. No. 14/057,920, filed Oct. 18, 2013, which is a continuation of International Patent Application No. PCT/GB2012/050853, filed Apr. 18, 2012, which claims the benefit of UK Patent Application No. GB 1106548.9, filed Apr. 18, 2011, the entire contents of which are hereby incorporated by reference.

The present invention relates to methods of investigating protein ligand binding interactions, in particular through the use of thermal shift analysis.

More particularly, the invention relates to methods for determining ligand binding to a non-purified target protein comprising steps of heating the non-purified target protein and ligand and analysing the product to detect soluble target protein. In certain embodiments, the methods of the invention use a separation step to separate soluble from insoluble proteins after heat treatment to estimate the amount of soluble target protein and thus thermally stable ligand bound target protein. In other embodiments, the methods of the invention use a detection method capable of distinguishing between soluble (e.g. folded or native) and denatured (unfolded) proteins (e.g. insoluble proteins) after heat treatment, e.g. a detection method based on the use of a pair of affinity reagents, such as antibodies, which may only recognise soluble folded target protein. The invention also relates to an instrument for use in the methods comprising a heating means, a means for separating soluble from insoluble protein and a means for analysing soluble or insoluble protein for the presence of target protein. The use of a kit comprising an antibody or a non-protein fusion tag in the methods of the invention is also described.

The detection of ligand binding to proteins is important in many different areas of biology and medicine. Particularly, during the development of chemical compounds into drugs, it is important to know if the compound interacts with the drug target. The monitoring of target protein-ligand interactions can therefore be used in initial screening for interacting ligands from large chemical libraries, as well as during optimization of an initial ligand into a candidate drug. Further, it is important to understand the interaction of a drug with other proteins (so called "off target interactions") where such interactions may result in side effects of treatments.

In other medical applications, it is important to determine whether a particular drug is able to bind its target protein in a patient or an animal model (for the disease). For a drug to be efficient, it needs to be absorbed in the stomach/gut (or if injected, it should enter the blood) and be transported to the right location in the body. If the drug is not targeted to an extracellular protein or receptor, the drug also needs to be transported into the cell in order to allow it to access the target protein. During all these transport processes, the drug needs to be stable and to avoid excretion from the kidney and degradation, e.g. in the liver or by cellular metabolic enzymes. The drug further needs to survive cellular drug resistance processes, such as degradation by P450 enzymes or translocation by multi-drug efflux channels. Finally, the drug needs to be able to bind to the drug target protein. Drug resistance in cancer and infection therapy is sometimes due to subtle mutations in the region of the drug-binding site on the target proteins.

However, in the path from drug to target, drugs will meet many different environments of the body and can potentially interact with many different proteins along the way.

The high complexity of the path for the drug before it reaches the binding site on the target protein is probably one reason why current predictive methods based on clinical diagnostics, expression profiling and sequencing only have limited success in predicting therapeutic efficiency. A potential means for measuring whether a drug has reached its target is to perform direct measurement of the drug-target protein interaction in the target cells of the body. Although this would not measure events downstream of the drug target, it would integrate all steps from drug to target as described above. Such measurements may therefore encompass many of the critical steps of therapeutic efficiency and would be a valuable predictor of the efficiency of many drugs and therefore as a clinical diagnostic tool. Thus, it is desirable to be able to detect ligand-protein interactions in non-purified samples e.g. those from patients, to study drug interactions and efficiencies.

Thermal shift assays have been developed in the art which can assess protein-ligand binding where the protein is in purified form. These assays have been developed on the basis of two principles, namely that a purified protein will melt and unfold at a particular temperature and that the binding of a ligand to a protein will thermally stabilise the protein. Thus, the binding of a ligand to a protein can be detected on the basis that the purified protein will show an increase in thermal stability once a ligand is bound and hence the protein will melt at a higher temperature once ligand is bound than purified protein alone. Vedadi et al. (PNAS, 103(43), 15835-15840, 2006) evaluated chemical screening methods to identify ligands that promote protein stability, crystallisation and structure determination. In these methods, the thermal stability of recombinant purified proteins was assessed after screening against small molecule libraries. An increase in protein thermal stability and thus ligand binding was measured using either fluorimetry (where fluorescent probes were used) or static light scattering. However, as discussed above, this method used purified proteins which melted at a particular temperature (as determined by a reference sample using unligated protein) allowing an increase in stability at the melting temperature to be measured.

Moreau et al. (Mol. BioSyst., 6, 1285-1292, 2010), recently used GFP as a reporter system to determine the stability of a target protein and its ligand-associated stabilisation, where GFP was fused to the target protein. However, this method is not ideal. Firstly, the method requires the construction and expressions of a fusion protein and can therefore not be used in natural cells and tissues but only in transformed cells. Further, the method can only be used to detect ligand binding to proteins which are less stable than GFP. Finally, the use of additives or salts affects the stability of GFP and thus a control GFP must be used for every experiment.

Thus, the thermal shift assays described in the prior art were only used in connection with purified protein, or in one case (Moreau et al., supra) in connection with a purified protein mixed with one other protein after purification where the protein is fused to GFP. In contrast to this, the inventors have developed an assay which can be used to determine binding of a ligand to a non-purified protein where the non-purified protein is not detected based on the enzymatic activity of any tag or peptide, polypeptide or protein fused thereto. Thus, the inventors have shown that it is possible for a non-purified protein e.g. in a cell, cell lysate or other complex liquid containing many different biomolecules, to unfold and precipitate with a characteristic temperature dependence, in a similar way to a purified protein. This discovery was unexpected since the conditions that are present in cells and in non-purified samples are quite different to the ones in a purified sample. Thus, in a non-purified sample or in a cell, it would be expected that several different processes may affect the solubility of a protein, which would act in parallel, such as different protein crowding effects or different chaperon or membrane interactions of partially unfolded proteins. The inventors used this finding as discussed above to develop a thermal shift assay, which can detect ligand binding to proteins in non-purified samples, based on the ability of non-purified proteins to melt at characteristic temperatures. The method is generic and can be used for most target protein and ligand combination, unlike the methods of the prior art. The assay investigates the thermal stability of the target protein in non-purified form at a particular temperature where an increase in thermal stability is indicative of ligand binding. Thus, the thermal stability of the non-purified target protein with added ligand is compared to the thermal stability of the non-purified target protein without ligand. Any increase in thermal stability of the non-purified target protein plus ligand compared to non-purified target protein without ligand indicates that ligand is bound to the non-purified target protein. Particularly, any increase in thermal stability is determined by detecting whether or not the target protein is soluble after heat treatment. In one embodiment, the assay of the invention therefore employs a simple step of separating soluble from insoluble proteins to identify any soluble target proteins. As discussed above such soluble proteins are associated with being thermally stable at the temperature applied to the sample and thus with having bound ligand. The separation step to discriminate between soluble and insoluble proteins thus allows the assay of the invention to be used to detect any target protein and therefore provides a generic method.

In an alternative embodiment, the assay of the invention uses a detection step which can distinguish between a soluble folded form of a target protein (alternatively viewed, a native protein) and the denatured or unfolded form (e.g. insoluble or precipitated form) of that target protein, and which may therefore not require the performance of a separation step (e.g. to separate soluble and insoluble proteins). In this embodiment, the detection step may employ affinity reagents, such as a pair of antibodies, to specifically identify the presence of the soluble folded form of a protein (or a native protein) against a background of the same protein in denatured (unfolded) and/or aggregated form and other proteins. The use of a detection step which is capable of distinguishing between both soluble or native and unfolded (particularly insoluble) forms of the same protein and the potential avoidance of separation is clearly advantageous. Such an assay has a minimal number of steps which allows the assay to be carried out in a high throughput format, e.g. in a microtiter based format, and further allows the assay to be used to visualise whether ligand-target protein interactions are occurring in tissue samples, e.g. by immunohistochemistry of tissue samples.

Therefore, in one aspect the invention provides a method for identifying a ligand which is capable of binding to a target protein wherein said target protein is non-purified comprising the steps of (a) exposing a sample comprising said non-purified target protein and a test molecule, to a temperature which is capable of causing or enhancing precipitation of said target protein
(b) processing the product of step (a) in order to separate soluble from insoluble protein and
(c) analysing the soluble proteins of step (b) for the presence of target protein, wherein said target protein is not detected on the basis of enzymatic activity of a tag, peptide, polypeptide or protein fused thereto.

Thus, as discussed above, the method of the invention is concerned with detecting ligand binding to a target protein in a non-purified sample where surprisingly a target protein in such a sample is capable of melting or unfolding with a characteristic temperature. When a target protein is bound to a ligand, the thermal stability of the target protein is generally increased and thus the target protein may melt at a higher temperature when ligand is bound than when no ligand is present. Applying a temperature to a sample which usually melts/unfolds unbound target protein may therefore result in unbound target protein being unfolded and target protein to which a ligand is bound remaining folded to a larger extent. The detection of higher levels of folded target protein is therefore indicative of ligand binding. Folded target proteins are generally soluble whereas unfolded proteins are generally insoluble. Hence, the solubility of a protein is linked to its thermal stability. Thus, the detection of higher levels of soluble target protein after heat treatment using a temperature at which the target protein usually start to precipitate and become insoluble indicates the presence of folded target protein with an increased thermal stability and hence ligand binding.

The invention is concerned with analysis of impure samples. This allows the technology to be used in a "biosensor" type method. Non-purified samples, in particular clinical or environmental samples, which may contain a ligand of interest can be analysed by adding the target protein to the sample, either as a purified protein or in a non-purified sample (e.g. as a cell lysate). Such methods allow quantification of the presence of a drug or other analyte in a serum sample, even though the target protein is originally not present in the serum. A cell lysate containing the target protein, e.g. from the target cells of the drug can be added to the clinical sample.

Thus, the present invention provides a more general method of determining whether a non-purified sample contains a target protein bound to a ligand of interest comprising the steps of:
(a) exposing said non-purified sample to a temperature which is capable of causing or enhancing precipitation of the unbound target protein to a greater extent than it is capable of causing or enhancing precipitation of the target protein bound to said ligand;
(b) processing the product of step a) in order to separate soluble from insoluble protein; and
(c) analysing either or both the soluble and insoluble protein fractions of step b) for the presence of target protein, wherein said target protein is not detected on the basis of enzymatic activity of a tag, peptide, polypeptide or protein fused thereto.

In a third aspect, the invention provides a method of determining whether a non-purified sample contains a target protein bound to a ligand of interest comprising the steps of:
a) exposing the non-purified sample to a temperature which is capable of causing or enhancing precipitation of the unbound target protein to a greater extent than it is capable of causing or enhancing precipitation of the target protein bound to the ligand; and b) analysing said sample for the presence of soluble or native target protein using two or more affinity reagents capable of binding to said soluble or native target protein with a higher affinity than to an unfolded and/or insoluble form of said target protein.

The analysis step b) allows the detection of the presence of any soluble or native target protein, which is indicative of ligand binding to the target protein.

In aspects where a highly specific antibody is available, it may be possible to employ the above method using only that specific antibody instead of the two or more affinity reagents which are capable of binding to said soluble or native target protein with a higher affinity than to an unfolded and/or insoluble form of said target protein. In that instance, step b) of the above method may be a step of analysing said sample for the presence of soluble or native target protein using one or more affinity reagents (antibodies) which are capable of specifically binding to said soluble or native target protein but not to unfolded and/or insoluble target protein. Such an antibody may be capable of detecting soluble or native target protein in a method as described above, without performing a separation step, if a signal attached or conjugated to the antibody is changed upon binding (e.g. fluorescence is emitted or the wavelength of the signal is altered). The skilled man is familiar with thermal shift analysis of purified proteins and the melting point curves produced thereby. The midpoint of the melting point curve may be taken to be the melting point of the protein and this temperature can change on ligand binding. It is appreciated that depending on the nature of the shift caused by ligand binding, at certain temperatures there may be some melting (precipitation) of both bound and unbound proteins but that precipitation occurs to a greater extent with the unbound protein. The temperatures at which the shift is visible and the amount of precipitated protein differs are discriminatory temperatures and temperatures within that range can be used as a single discriminatory temperature according to step (a) above. That is particularly so when the m.p. of unbound and bound target proteins are known and the method is performed as an assay for the presence of target protein and/or ligand in the sample. Thus ligand may be added to a sample to confirm the presence of target protein.

The method of the invention is a generic method for determining ligand-target protein binding in a non-purified sample. Unless otherwise clear from the context, discussion herein of "non-purified protein" applies *mutatis mutandis* to 'non-purified samples'. This method has many advantages over the methods of the art. Firstly, it abrogates the need to purify proteins in order to investigate ligand binding. Further, the method does not require the recombinant expression of target protein or the production of a protein containing a fusion reporter protein (such as in Moreau et al., supra). It further allows the investigation of ligand binding in cell culture, animal or patient samples which was not previously possible using thermal shift binding assays. As discussed above, this is important for analysing whether a particular drug can be efficiently used to treat disease in a particular patient and to assist in determining optimal dosage of the drug. For example, this has important ramifications for the treatment of cancer and infectious diseases, where drug resistance often can occur. In such cases being able to detect patients who would not be effectively treated with the drug, allows other therapies to be commenced, or drug dosage to be adjusted.

Further, the detection steps of the method of the invention do not require the use of expensive equipment or machinery; indeed, the separation step of the first two embodiments can be achieved using a filter and target protein detected for example using antibodies. The method can be used for any protein to detect the binding of a ligand; there is no requirement to design specific probes etc for each protein to be detected in the method. Thus, the method of the invention represents an efficient, reliable way of determining protein-ligand binding in a non-purified sample. Additionally, as discussed further below, the method can be easily multiplexed and used to screen libraries of ligands or proteins for interaction. In the third embodiment, as discussed previously, separation is not required (although can be performed if desired) and detection of soluble or native target protein is carried out using two or more affinity reagents which are capable of binding to soluble or native target protein and of distinguishing between soluble or native and unfolded and/or insoluble forms of a target protein. The term "target protein" as used herein, refers to a protein which is being assessed in the method of the invention for ligand binding. The target protein can therefore be any protein which is present in a sample. The target protein may be naturally occurring e.g. in a cell or cell lysate or animal or patient sample or may be recombinantly expressed e.g. may be expressed from a plasmid which has been transformed into a cell. As mentioned above, the target protein may not initially be present in the sample but may be added thereto to investigate the presence of ligand in the starting sample. Thus, according to the present invention, the 'sample' is the test sample which is treated in step (a) and this may be different from the starting sample, e.g. the clinical sample. Likewise, ligand may be added to the starting sample. Additions of known amounts of target protein or ligand may assist in obtaining quantitative data.

The target protein may be in wildtype form i.e. as it usually occurs in nature or may comprise one or more mutations. Thus genes/cDNA/coding regions encoding a protein can be mutated to produce variants of that protein e.g. mutants with varying abilities to bind the ligand. As discussed further below, these mutants can be produced in an expression system wherein the variants, which for example have increased ligand binding, can be selected using the methods of the invention.

Typically, the target protein will have a native or native-like conformation and will be soluble. Native or native-like proteins are expressed in soluble form and/or correctly folded. Native-like membrane proteins do not have to be present free in solution, but may be present in cellular membranes or membrane vesicles rather than inclusion bodies. Thus native-like proteins are generally not insoluble, present in inclusion bodies, aggregated or misfolded. Particularly, the method of the third embodiment may be used for analysing ligand binding to target proteins which are membrane proteins, e.g. which are present in intracellular membranes.

The target protein may exist in the form of numerous variants across an animal population. These variants may exist within a healthy animal population, or the variation in the protein may lead to disease or drug resistance within a population. The methods of the invention provide a means of screening a ligand across a range of different target protein variants. Such information may be useful in order to develop ligands that bind to certain protein variants specifically, or to determine which form of therapy may be most adequate for a patient based on the protein variant which they naturally express. Thus, the method may be repeated with two or more target proteins, those target proteins being variants of the same protein.

A "soluble protein" can be defined in reference to possession of a native or native-like conformation. A soluble protein may be correctly folded. Further, a soluble protein can be described as a protein which remains in the supernatant after centrifugation of a sample (with a prior lysis step if said protein is within a cell. Centrifugation can typically be carried out between 100 g and 20000 g. The duration of centrifugation can be from 1 minute (typically at least 10 minutes) to at least 1 hour, where the duration required generally decreases as the centrifugal force increases. Particularly suitable conditions for providing only soluble proteins in the resultant supernatant include 30 minutes at 3000 g or 15 minutes at 20000 g.

An "unfolded protein" may have an unfolded or at least partially unfolded conformation compared to the native form of the protein. Such a protein will generally also be insoluble but in some instances, unfolded proteins may remain in solution.

An "insoluble protein" can be identified in reference to having an unfolded or at least partially unfolded conformation compared to the native form of the protein. Generally, an insoluble protein will be precipitated from solution and may be separated from a solution (or supernatant) by performing a separation step such as that described above e.g. by centrifugation.

The term "non-purified target protein" refers to the target protein when not in isolated form or alternatively viewed when present with other compounds e.g. proteins. The non-purified target protein to be used in the methods of the invention are in non-purified form before the addition of the test molecule (potential ligand) or in the absence of the test molecule. Thus, the non-purified target protein is present with compounds other than the test molecule (potential ligand) which is tested to determine whether or not it is a ligand for the target protein. The non-purified target protein thus includes target protein when comprised within or on cells, cell lysates and samples obtained directly from patients (human patients or animal patients or disease models e.g. dog, cat, monkey, rabbit, mouse, rat, etc.) such as tissue samples, blood, serum, plasma, lymph, etc. The non-purified target protein includes target protein when comprised in one or more cell colonies, where a cell colony is defined as a circumscribed group of cells, normally derived from a single cell or small cluster of cells growing on a solid or semi-solid medium (i.e. culture media with the addition of 0.1% or greater agar). The non-purified target protein may also be comprised in a liquid culture of cells. A liquid culture of cells may comprise cells which have all originated from a single cell i.e. the cells within the liquid culture may be clonal, or the liquid culture may comprise a suspension of different cells. The cells of the colonies or in liquid culture may be prokaryotic i.e. bacteria or eukaryotic cells e.g. yeast, unicellular eukaryotes such as Leishmainia, insect cells or mammalian cells or cell lines. Cells in liquid culture or grown as colonies may be formed as *E. coli, Bacillus subtilis, Streptococcus lactis, Streptococcus lividens, Lactococcus lactis, Staphylococcus aureas, Aspergillus niger, Picia pastoris, Saccharomyces cerevisiae* or *Schizosaccaromyces pombe*. All of the above are examples of a sample comprising a target protein.

As mentioned above, key to the present invention is the finding that 'dirty' samples can yield reliable information when undergoing thermal shift analysis. Thus, the sample at (a) is non-purified but there may be circumstances where a purified target protein has been added to a dirty starting sample. The sample is not purified and contains components such as other proteins, cell debris, nucleic acids etc., as described herein in the context of "non purified target protein".

Typically, a non-purified target protein has not been subjected to a purification process which would result in the purification of the target protein. Such a purification process may comprise of several steps and thus the non-purified target protein used in the present invention has not been subjected to all such necessary steps to produce a purified protein. For example where the protein is present in a tissue, steps of extraction, precipitation and separation e.g. by centrifugation or chromatography may be used to purify the protein. The non-purified target protein of the present invention would not be subjected to all such steps and thus a purified target protein would not be isolated. It is possible that the non-purified target protein could have been subjected to one or more steps e.g. the extraction step of a purification process, as long as the purification process was not completed and a purified protein was not isolated. The non-purified target protein is therefore typically present with other compounds or proteins and thus the target protein is not present in isolated form.

The term "test molecule" as used herein refers to any molecule or compound, which is tested in the methods of the invention to determine whether or not it is a ligand for the target protein. Alternatively viewed, the test molecule is a potential ligand for the target protein. Thus, the test molecule or ligand may be a protein, polypeptide, peptide, RNA, or DNA molecule. In a particular embodiment, the molecule/ligand may be a drug or pharmaceutical product, a cell metabolite or a hormone e.g. in serum. The test molecule or ligand may be naturally occurring or may be synthetically or recombinantly produced, using any of the methods already described or discussed further below.

The test molecule used may or may not bind to the target protein; in one aspect the method of the invention determines or assesses whether a particular molecule or compound is capable of binding to the target protein i.e. whether a test molecule or compound is a ligand. Thus, the invention can be used to screen a small molecule library for molecules which are capable of binding to the target protein. Some of the molecules tested may not bind, whereas others may bind to the target protein. Additionally, the method of the invention can be used to identify variants of small molecules known to bind to the target protein, which can bind the target protein with higher affinity (or alternatively with lower affinity) where this is often reflected in the degree of thermal stabilization. Thus, test molecules can be mutated ligands or known (or unknown) target protein binding partners. The production of such mutated molecules is achieved by using any of the mutation processes described herein.

Thus, in one aspect, the present invention provides a method for identifying a ligand capable of binding to a target protein comprising the steps of:
(a) exposing a non-purified sample comprising said target protein and a test molecule to a series of different temperatures, including a temperature which is equal to or greater than the initial melting temperature of the target protein;
(b) processing the products of step a) in order to separate soluble from insoluble protein and
(c) analysing either or both the soluble and insoluble protein fractions of step b) for the presence of target protein, wherein said target protein is not detected on the basis of enzymatic activity of a tag, peptide, polypeptide or protein fused thereto.

In a further aspect, the invention provides a method for identifying a ligand capable of binding to a target protein comprising the steps of:

(a) exposing a non-purified sample comprising said target protein and a test molecule to a series of different temperatures, including a temperature which is equal to or greater than the initial melting temperature of the target protein; and
(b) analysing said sample for the presence of soluble or native target protein using two or more affinity reagents capable of binding to said soluble or native target protein with a higher affinity than to an unfolded and/or insoluble form of said target protein.

The term "ligand" as used herein refers to a test molecule or more generally to a compound which is capable of binding to the target protein. A target protein may have a co-factor or physiological substrate bound thereto but methods of the invention investigate the melting point of a target protein bound to a ligand of interest as compared to the target protein when not bound to that ligand (unbound target protein). The ligand of interest may bind elsewhere on the protein or may compete for binding e.g. with a physiological ligand. Ligands of interest may be drugs or drug candidates or naturally occurring binding partners, physiological substrates, etc. Thus, the ligand can bind to the target protein to form a larger complex. The ligand can bind to the target protein with any affinity i.e. with high or low affinity. Generally, a ligand which binds to the target protein with high affinity may result in a more thermally stable target protein compared to a ligand which binds to the target proteins with a lower affinity. Typically, a ligand capable of binding to a target protein may result in the thermal stabilisation of that target protein by at least 0.25 or 0.5° C. and preferably at least 1, 1.5 or 2° C.

Hence, when a test molecule is already known to bind the target protein (and thus is a ligand for the target protein), the method of the invention can be used to assess the binding of the ligand to the target protein e.g. to determine the strength of the interaction. In this aspect, the invention provides a method for assessing ligand binding to a target protein wherein said target protein is non-purified comprising the steps of a) exposing a sample comprising said target protein and said ligand, to a temperature which is capable of causing or enhancing precipitation of said target protein, b) processing the product of step a) in order to separate soluble from insoluble protein and c) analysing the soluble proteins of step b) for the presence of target protein wherein said target protein is not detected on the basis of enzymatic activity of a tag, peptide, polypeptide or protein fused thereto.

Alternatively, the invention provides a method for assessing ligand binding to a target protein wherein said target protein is non-purified comprising the steps of a) exposing a sample comprising said target protein and said ligand, to a temperature which is capable of causing or enhancing precipitation of said target protein, and b) analysing said sample for the presence of soluble or native target protein using two or more affinity reagents capable of binding to said soluble or native target protein with a higher affinity than to an unfolded and/or insoluble form of said target protein.

In order to assess or determine ligand binding to a non-purified target protein or to identify a ligand for a non-purified target protein, the test molecule or ligand is typically added to the sample. However, it is possible that the test molecule or ligand is already present in a sample comprising the non-purified target protein e.g. is naturally occurring. Thus the invention may also provide a method for identifying a ligand which is capable of binding to a target protein wherein said target protein is non-purified comprising the steps of (ai) adding a test molecule to said non-purified target protein
(a) exposing the product of step (ai) to a temperature which is capable of causing or enhancing precipitation of said target protein
(b) processing the product of step (a) in order to separate soluble from insoluble proteins and
(c) analysing the soluble proteins of step (b) for the presence of target protein wherein the presence of the target protein indicates that said molecule is bound to said target protein and is a ligand capable of binding to said target protein and wherein said target protein is not detected on the basis of enzymatic activity of a tag, peptide, polypeptide or protein fused thereto.

Alternatively, the invention also provides a method for identifying a ligand which is capable of binding to a target protein wherein said target protein is non-purified comprising the steps of (ai) adding a test molecule to said non-purified target protein
(a) exposing the product of step (ai) to a temperature which is capable of causing or enhancing precipitation of said target protein and
(b) analysing said sample for the presence of soluble or native target protein using two or more affinity reagents capable of binding to said soluble or native target protein with a higher affinity than to an unfolded and/or insoluble form of said target protein
wherein the presence of soluble or native target protein indicates that said molecule is bound to said target protein and is a ligand capable of binding to said target protein.

Typically, where the test molecule (potential ligand) is present extracellularly e.g. in solution, this may be simply added to the non-purified target protein e.g. mixed together with the non-purified target protein where this is also in solution or dropped onto the target protein e.g. where the target protein is present in an aliquot of harvested cells. Alternatively, the test molecule (potential ligand) may be expressed recombinantly from a vector encoding the test molecule. The step of adding the test molecule may therefore involve transforming or transfecting a cellular sample with the vector encoding the test molecule and/or inducing expression of the test molecule from the vector in a cellular sample once transformation or transfection has been carried out. The step of adding the test molecule further includes inducing expression of a test molecule encoded by a gene naturally occurring in a cellular sample.

Further, where the target protein is present within a cell, the method may require an extracellular test molecule or ligand to be transported into the cell to contact the target protein. For test molecules or ligands which bind to a target protein on the cell surface however, there is no need for transport into the cell. The invention may therefore provide a method of determining whether a non-purified sample contains a target protein bound to a ligand of interest comprising the steps of a) exposing the non-purified sample to a temperature which is capable of causing or enhancing precipitation of the unbound target protein to a greater extent than it is capable of causing or enhancing precipitation of the target protein bound to said ligand, wherein the target protein in said non-purified sample is comprised within or on a cell and b) analysing said sample for the presence of soluble or native target protein using two or more affinity reagents capable of binding to said soluble or native target protein with a higher affinity than to an unfolded and/or insoluble form of said target protein.

Alternatively, or additionally, where the target protein is present in a cell (or on the cell surface), a step of lysis may be carried out before, simultaneously or after the test molecule or ligand has been added. Such a lysis step allows contact between the target protein and the test molecule or ligand and/or the later assessment of any binding between the test molecule or ligand and target protein. Thus, any necessary lysis step is generally carried out before the separation step of the method of the invention. Alternatively, in methods where a separation step is not carried out, any lysis step may generally take place before the analysis/detection step, particularly between the heating and analysis/detection step. However, in particular embodiments, in methods where detection is carried out using two or more affinity reagents which are capable of binding to the soluble or native form of the target protein with higher affinity than to the unfolded and/or insoluble form of the target protein, a lysis step may not be carried out, e.g. where cellular interactions are to be directly visualised. It will be apparent that a step of lysis may only need to be carried out on samples where the target protein is comprised within a cell. The lysis step may be thermal dependent i.e. the lysis may only occur at a particular temperature e.g. at the end of a thermal cycle.

The lysis step of the present invention will have different requirements depending on whether the cells are subjected to heat treatment before or after any lysis step. For cells subjected to lysis before heat treatment, preferably, the lysis step is non-denaturing, allowing target proteins to retain a native i.e. correctly folded or native-like conformation. This is referred to herein as native lysis. This can be carried out chemically or otherwise using reagents which are well known in the art e.g. urea, lyzozyme containing buffers or detergents. The degree of lysis must be sufficient to allow proteins of the cell to pass freely out of the cell. Typically, when dealing with membrane bound proteins, lysis is performed in the presence of detergents or amphiphiles, for example Triton X-100 or dodecylmaltoside, to release the protein from the membrane. The lysis step can alternatively be carried out by freeze thawing the cells or colonies. More preferably, lysis is carried out using both native lysis buffer and freeze thawing the cells. Preferably, the lysis buffer contains lysozyme, for examples at 50-750 µg/ml, more preferably at 100-200 µg/ml. DNAse can also be found in native lysis buffer preferably at 250-750 µg/ml. Native lysis buffer may contain for example 20 mM Tris, pH 8, 100 mM NaCl, lysozyme (200 µg/ml) and DNAse I (750 µg/ml). For target proteins known to be inserted into cellular membranes, detergents would be added to the lysis buffer at typical concentrations where they are known to solubilise membrane-inserted proteins in a native form, such as 1% n-dodecyl-β-maltoside. Typically, the cells will be exposed to the lysis buffer for 15-60 minutes, preferably around 30 minutes. The step of freeze thawing is preferably repeated, i.e. two or more cycles, preferably 3 or more cycles of freeze thawing are performed. In one preferred embodiment lysis is achieved by a 30 minute incubation at room temperature with lysis buffer and three ×10 minutes freeze thawing.

Typically, the percentage of cells lysed within a sample (e.g. a cell colony or cell culture) during the lysis step is 5-100%. Thus, it is not necessary when performing a step of lysis for all cells within a sample to be lysed. Only a small percentage are required to be lysed in order to release sufficient target protein to either contact with ligand and/or to be subjected to the separation step.

As discussed briefly above, it is possible that the test molecule or ligand is already present in a sample comprising the target protein. In this instance it may be possible to investigate natural ligand binding to a target protein e.g. by diluting the sample with buffer and detecting any negative shift in thermal stability of the target protein when a ligand is released.

The methods of the invention require that the non-purified sample is exposed to "a temperature which is capable of causing or enhancing precipitation of said target protein". This refers to a temperature which is capable of causing or enhancing precipitation of target protein in the absence of the test molecule (potential ligand). Likewise the non-purified sample is exposed to "a temperature which is capable of causing or enhancing precipitation of the unbound target protein to a greater extent than it is capable of causing or enhancing precipitation of the target protein bound to said ligand". "Unbound" refers to the target protein when not bound to, i.e. in the absence of, the ligand of interest.

Thus, as discussed previously, the inventors have found that proteins in non-purified form generally precipitate with a particular temperature dependence, (i.e. having distinct melting temperatures) in a similar manner to purified proteins, despite the varying conditions found within non-purified samples and particularly within cells. Therefore, the protein may precipitate over a small temperature range. Occasionally, some proteins may undergo several transitions in their state during heating over a temperature range indicating that there are several forms of the protein present in the sample (e.g. different spliced forms, phosphorylated forms, or bound to other proteins). In this situation, it is possible that a test molecule/ligand will not bind to all forms of the protein in all transition states. Hence, a test molecule or ligand may only bind protein in one or more of its transition states. Thus, it is possible that a test molecule/ligand may only be able to thermally stabilise certain transition states or forms of the protein and thermal shifts in the stability will only be seen for these transition states.

Where a target protein precipitates over a small temperature range, the initial melting temperature is the first temperature in the range and the final melting temperature is the last temperature in the range. Thus, the initial melting temperature is the lowest temperature at which target protein begins to precipitate e.g. at least 5% of the target protein is precipitated and the final melting temperature is the first temperature at which no soluble target protein is detected, e.g. less than 5% of target protein is in soluble form. Typically, at least 95% of target protein is melted and precipitated.

Therefore, when a target protein precipitates over a temperature range, the target protein may begin to precipitate or unfold at a particular temperature at which point the amount of soluble target protein present will begin to decrease and the amount of insoluble target protein present will increase (since thermal stability is linked to solubility). Therefore, some soluble protein may still be detectable at the initial melting temperature until a slightly higher temperature is applied, at which point little or no soluble protein is detectable.

The final melting temperature for a protein is therefore a particular temperature at which there is a significant decrease of soluble protein detected, typically at least 95% of the protein is insoluble. For problematic proteins having multiple transitions, each of these transitions may result in a smaller amount of protein becoming insoluble, but this would still be significant enough to be measured (e.g. at least 10% of the protein becomes soluble at each transition). Where the protein precipitates over a small temperature range, where the percentage of soluble protein decreases until no soluble protein is detectable and thus the protein is completely unfolded or precipitated, an initial and final melting temperature can be determined. Hence, at the initial melting temperature of such a temperature range i.e. the lowest temperature at which target protein begins to melt or precipitate, at least 5, 10, 15, 20, 25, 30, 35, 40, 45, 50, 55, 60, 65, 70, 75, 80, 85, 90 or 95% of the target protein may melt or precipitate. Alternatively viewed, at the initial melting temperature of a temperature range, the amount of soluble target protein detected decreases by at least 5, 10, 15, 20, 25, 30, 35, 40, 45, 50, 55, 60, 65, 70, 75, 80, 85, 90 or 95%. Further, the amount of insoluble target protein present may increase by at least 5, 10, 15, 20, 25, 30, 35, 40, 45, 50, 55, 60, 65, 70, 75, 80, 85, 90 or 95%.

It is also possible that a target protein may unfold and precipitate at one specific temperature. In this instance, preferably at least 95% of the target protein will be in insoluble form at a specific temperature and hence the protein may not precipitate over a small temperature range. The initial melting temperature for such proteins may therefore be close to the final melting temperature.

The temperature which can be applied in the present invention may be any temperature from the initial melting temperature at which the target protein begins to unfold. Any temperature equal to or higher than the initial melting temperature will be capable of causing or enhancing precipitation of the target protein. Thus, a target protein with a higher thermal stability due to ligand binding will generally not unfold or precipitate at this temperature and a higher amount of soluble protein will be detected as compared to target protein alone which has either completely unfolded or begun to unfold. The temperature is thus discriminatory, causing or enhancing precipitation of the unbound target protein to a greater extent than it causes or enhances precipitation of the target protein bound to the ligand of interest.

The detection of an increased amount of soluble target protein at a particular temperature when a test molecule is present as compared to the amount of soluble target protein present when the test molecule is absent is indicative that the molecule is a ligand for the target protein and that the test molecule is bound to the target protein. Where the temperature used in the present invention is the initial melting temperature or a temperature between the initial melting temperature and the final melting temperature (i.e. not a temperature which results in at least 95% of the target protein being insoluble (the final melting temperature or a higher temperature than this)) it may be necessary to carry out a control reaction simultaneously for target protein without ligand present, in order to compare the amounts of soluble protein detected in both cases, to detect the samples with ligand where an increased amount of soluble target protein is present compared target protein alone. This is typically done by measuring the melting curve of the protein in similar non non-purified samples. However, where a temperature is used in the invention at which no or very little soluble target protein is detected (i.e. target protein without ligand) e.g. the final melting temperature, there is no need to use a comparison or control for every measurement. In this case, any detection of soluble protein in the method indicates the presence of a thermally stable and hence ligand bound target protein. Such a temperature would typically be equal to or higher than the final melting temperature.

Additionally, the temperature can be chosen in the present invention to screen for only ligands which bind to the target protein with a high affinity. Thus, typically the higher the temperature at which soluble proteins and hence thermally stable ligand bound target proteins are detected, the higher the affinity of the ligand binding to the target protein is likely to be. Hence, if only high affinity interactions are required to be detected, a temperature which is higher than the final melting temperature can be selected e.g. 3, 4, 5, 6, 7, 8, 9, 10 or more ° C. higher than the final melting temperature. Thus, preferably, the temperature selected would be higher than the final melting temperature of a temperature range. Alternatively, if it is desired to identify all molecules/ligands bound to the target protein, a lower temperature can be used, for example one equal to the initial melting temperature of a range. Alternatively viewed, when selecting for high affinity interactions, the discriminatory temperature of step (a) will be one which causes or enhances precipitation of unbound target protein to a much greater extent than it causes or enhances precipitation of the ligand bound target protein, e.g. at least 30% more, preferably at least 50% more, more preferably at least 60, 70 or 80% more.

The binding affinity of the ligand to the target protein can be determined through performing the method steps described above at a range of varying ligand concentrations or target protein concentrations. In such methods, the sample treated in step (a) will have added thereto a known amount of target protein or ligand. One can plot a dose-response curve, and therefore determine the binding constant of the ligand (i.e. the concentration of ligand or target protein at which half of the target protein is bound to ligand). Such binding information obtained in a clinical, impure sample would provide a more accurate interpretation of the binding characteristics of the ligand to the target protein under physiological conditions compared to information derived from pure samples. Such information could have useful applications to set dosing regimes for patients or to find a therapeutic window for a drug by studies of apparent binding constants in different organs of the body. Thus, certain aspects of the invention may also comprise a further step:

d) repeating steps a) to c) with one or more (e.g. 2 or more, preferably 3 or 4 or more) different concentrations of ligand or target protein.

The heating step can be carried out using any heat source which can heat a sample to a particular temperature. Thus, where the non-purified target protein and test molecule (potential ligand) are in liquid form, then preferably the heating step may be carried out in a PCR machine. However, incubators, waterbaths, etc. may also be used. Where the target protein is in a cell colony, an incubator is preferably used to carry out the heating step.

The invention further encompasses applying a range of temperatures to the target protein and test molecule and processing and analysing the target protein after incubation at each temperature in order to produce a precipitation curve for each target protein and test molecule combination. Thus, a target protein and ligand may be incubated at any temperature range as long as one temperature is used which is capable of causing or enhancing precipitation of the target protein (i.e. without bound ligand). Preferably therefore, the temperature range applied includes incubating at the initial melting temperature or at a temperature higher than the initial melting temperature. By incubating the non-purified target protein and test molecule at a whole range of temperatures, it is possible to determine the temperature at which the target protein precipitates when ligand is bound. Further, if a control of non-purified sample without ligand is subjected to the same temperature incubations, it is possible to identify ligand bound protein samples without prior knowledge of the target protein melting temperature. Preferably, any such heating of a control would be carried out simultaneously to the heating of the non-purified sample and test molecule/ligand. By using a precipitation curve, it is also possible to determine ligands which have the greatest effect on thermal stability when more than one ligand is being investigated.

Typically a temperature range may be used to produce a precipitation curve where the temperatures used are about 2, 3, 4, 5, 6, 7, 8, 9 or 10° C. different from one another. Thus the target protein and test molecule could be incubated at any one of more of 27, 30, 33, 36, 39, 42, 45, 48, 51, 54, 57, 60, 63, 66, 69, 72 and 75° C. as long as one of the temperatures is equal to or higher than the initial melting temperature for the target protein. Where the target protein and test molecule are heated over a temperature range, this can be carried out in a PCR machine where an initial temperature can be set and then increased by the desired amount after a particular amount of time e.g. 1, 2, 3, 4 or 5 minutes. As discussed previously, a small aliquot or amount of sample (e.g. 1 or 2 μl) can be removed after heating at each temperature in order that the solubility of the target protein can be analysed. Where the non-purified target protein is present in one or more cell colonies, a portion of the colony may be lifted off after each incubation e.g. by placing filter paper on the top of the colony.

In order to apply the method of the invention, it is necessary to determine the melting temperature(s) of the target protein of interest without test molecule/ligand so that any thermal shift in the presence of test molecule/ligand can be detected. Thus, the melting temperature(s) of the target protein can be determined before the method of the invention is carried out or a simultaneous control reaction can be carried out with the method of the invention where a range of temperatures are applied to the control and to the target protein and molecule e.g. as discussed above to produce a precipitation curve. The Tms (temperature at which 50% of protein is precipitated) of many target proteins in purified samples are also known in the art and although the Tms for non-purified target proteins are slightly different, these can often be used as a guide for the melting temperatures of non-purified proteins.

"A temperature capable of causing or enhancing precipitation" of target protein therefore refers to a temperature or a temperature range as discussed above at which there is an increase in the precipitation or alternatively viewed the unfolding or melting of a target protein as compared to target protein at a lower temperature. The temperature is generally an increased temperature compared to the temperature at which the target protein is usually found e.g. 37° C. for target proteins within a patient. Thus the temperature applied is typically above 37° C., preferably above 40° C., e.g. above 50° C.

The temperature used in the invention thus preferably causes an increase in precipitation of the target protein by at least 5, 10, 15, 20, 30, 40, 50, 60, 70, 80, 90 or 95%. An increase in protein precipitation usually results in insoluble protein being produced and thus alternatively viewed, the temperature used in the invention may cause an increase in the amount of insoluble target protein present e.g. an increase of at least 5, 10, 15, 20, 25, 30, 35, 40, 50, 60, 70, 80, 90 or 95%. In the present invention, any enhancement of precipitation may be measured by measuring a decrease or reduction in the amount of soluble target protein present e.g. a reduction of at least 5, 10, 15, 20, 25, 30, 35, 40, 50, 60, 70, 80, 90 or 95%. Measurement of this decrease could for example be done using dot-blots or ELISA-experiment where the amount of bound antibody can be quantified using e.g. integration of fluorescence signals of florescence labelled antibodies.

In one aspect, the method of the invention further requires the use of a separation step (b) to separate soluble from insoluble proteins. The separation step can involve any separation method which is capable of separating soluble from insoluble protein. For example, a step of centrifugation can be used as described above or in a preferred embodiment, a step of filtration may be used. Thus, a filter can be used to separate soluble from insoluble proteins where soluble proteins will pass through a filter. Standard filter membranes can be used for filtering heated samples where the filters will typically have a pore size from 0.015 μm to 12 μm, preferably from 0.35 to 1.2 μm, more preferably from 0.45 μm to 0.8 μm. Preferably the filters have pore sizes below 4.0 μm, typically below 2.0 μm, more preferably below 1.0 μm. When the target protein is produced or expressed in cells, such as bacteria e.g. *E. coli*, an optimal pore size may be 0.1-1.5 μm. Where is target protein is from a eukaryotic cell or sample, preferred pore sizes may be larger. It will be appreciated that filters are manufactured and marketed as having a particular pore size but the manufacturing process may occasionally result in a few smaller or larger pores; the sizes listed, which refer to the diameter, are thus the most common pore size of a given filter. Although reference is made to a range of potential pore sizes, any single filter will usually have one designated pore size e.g. 0.45 μm. Suitable filters are Super and GH polypro (from Pall) and Nucleopore (from Whatman).

It will be appreciated that target proteins from eukaryotic and prokaryotic samples and from different cell types may require the use of filters with different pore sizes. Selection of a suitable filter is well within the competency of someone skilled in this field. For example, it is possible to select an appropriate pore size, by using a set of test proteins for the desired cell type or sample and investigating their behaviour with filters of varying pore sizes.

As discussed previously, where the target protein is present within a cell, a step of cell lysis may be carried out prior to the separation step when this is carried out or prior to the analysis/detection step. Cell lysis will also be required when the sample is a cell sample and target protein is added thereto in order to assay for the presence of a ligand. When the present method is carried out on cell colonies, the lysis may be carried out directly on those colonies i.e. there is no need to pick the colonies and grow them in liquid culture (although this can be done). In this instance, it is preferred that the separation step is one of filtration. Further, where the method is performed on cell colonies, preferably, the filter paper is overlayed on the colonies to lift the colonies from the semi-solid or solid growth media. Alternatively, filters could be placed on the growth media and cells seeded directly onto the filter, the filter could then simply be lifted off with the colonies already on it. Preferably, the lifting of the colonies in this way can be carried out prior to the lysis step. As indicated above, the lysis can be carried out directly on the colonies on a filter. The filter with colonies attached can be treated with lysis buffer or overlaid on other membranes/filters treated with lysis buffer.

Filtration can also be carried out for liquid cultures of cells e.g. liquid cultures growing in a multi well plate e.g. a 96 well plate.

Filtration is carried out after any necessary lysis step is performed. It will be appreciated however that filtration and lysis may occur simultaneously when considering a whole colony since some cells may undergo lysis before others and hence may be filtered before or at the same time as others are lysed.

Preferably, where the separation step is filtration, proteins which pass through the filter are held on a solid support, e.g. a capture membrane, to allow screening/detection of the target protein(s) and then to allow the identification of sample(s) containing the target protein bound to ligand. Such capture membranes may typically comprise nitrocellulose. However, it will be appreciated that it is the first filter that separates soluble from insoluble protein in this method. In a preferred embodiment, proteins can simply be allowed to pass through the filter, possibly as a result of capillary action. In another embodiment, force may be applied vertically on the filter paper, wherein such forces can include the application of pressure or vacuum.

The capture membrane can fix the soluble proteins from the individual sample(s) and in this way, it is possible to multiplex this method. Thus, the positions of the target protein(s) on the capture membrane can be compared to the filter which either carries the original cell colonies, if the method is being carried out on cell colonies, or the sample spots. Thus, from the filtration blot, it is possible to track back and identify the original samples comprising the target protein and bound ligand. To aid in the process of identifying colonies comprising target protein bound to ligand, positive controls can be used. These are clearly seen on the final colony filtration blots and can enable the membrane/blot to be correctly orientated with the original colonies. Hence, after any filtration step is carried out, a solid support such as a capture membrane allows the ready identification of samples having target protein bound to ligand.

In another embodiment, the filter with heat treated sample(s) can be placed sample side down and a (nitrocellulose) capture membrane can then be placed on top of the filter and several layers of filter paper (and paper towels) can be placed on top of this. Force can then be applied to the top of this "sandwich" and ideally transfer buffer poured around the bottom to facilitate filtration and transfer of proteins onto the capture membrane.

In another embodiment, the filter is placed sample side up onto a capture membrane and a vacuum is applied to "pull" protein through the filter paper and onto the capture membrane.

Alternatively to filtration and centrifugation, affinity capture of soluble protein can be carried out. Many antibodies and affinity reagents that recognise the folded structure of the protein will bind the soluble protein with much higher affinity than the unfolded and precipitated protein. Thus, the use of affinity reagents that bind to the soluble or native target protein with a higher affinity than to the unfolded and/or insoluble target protein can negate the use of a physical step of separation in the method of the invention. Also the recognition of smaller tags such as poly-Histidine tags binding to metal conjugates will often correlate with solubility when these tags are less accessible in the precipitated protein. Antibodies, metal conjugates and other affinity reagents can be linked to magnetic beads or column resin which is mixed with the heat treated non-purified sample. This mix can in a subsequent step be put in an appropriate valve and washed to remove insoluble protein when this does not have high affinity to the affinity reagent. The amount of protein bound to the affinity reagent, can subsequently be measured using for example Bradford techniques, gel electrophoresis, Elisa or surface plasmon resonance detection.

According to the methods of the invention, which employ a separation step, it is possible to analyse either (or both) the insoluble or soluble fractions for the presence of target protein. The insoluble fraction is preferably solubilised prior to analysis, for example, as described in Example 3, the precipitated proteins may be dissolved in loading buffer prior to application to the separation gels. Preferably the methods of the invention which employ a separation step, also involve a step (c) of analysing the soluble proteins for the presence of target protein. Thus, the soluble proteins obtained after the step of separation are preferably analysed for the presence of target protein. Hence, if a centrifugation separation step was carried out, the supernatant can be analysed for the presence of target protein and where a filtration separation step was carried out, the proteins which pass through the filter i.e. the filtrate can be analysed for the presence of target protein.

In methods where a separation step is employed, the target protein can be detected by various different methods. Thus, target proteins can be detected using various tags which are well known in the art, e.g. histidine tag, VS tag, T7 tag, FLAG tag or any short protein sequence to which a specific antibody is available, thioredoxin and maltose binding protein. Tags are preferably between 1-100 amino acids in length, preferably between 1-70, 2-50, 1-30 or 1-20 amino acids in length. More preferably, tags can be 3, 4, 5, 6, 7, 8, 9 or 10 amino acids in length. However, the target protein is not detected on the basis of any enzymatic activity of a tag, peptide, poylpeptide or protein which is fused to the target protein. Thus, target proteins are not detected using an enzymatic activity exhibited by any such tags or proteins fused to the target protein, e.g. where the enzymatic activity results in the production of a detectable signal. For example, fusion tags that possess enzymatic activity such as green fluorescent protein, horseradish peroxidase, luciferase and glutathione-S-transferase are not used in the present invention to detect the target protein. Thus, although it is possible for any tag/protein to be fused to the target protein, the target protein is not detected using the enzymatic activity possessed by any such tags or proteins. Thus, in the case of a GFP tag, fluorescent green light is produced by an enzymatic reaction and hence it is specifically excluded in the present invention, for a target protein to be detected using such a reaction. Hence, the detection of the target protein by fluorescence produced from a GFP tag is excluded, since such fluorescence is the result of enzymatic activity possessed by the tag. Further, in a preferred embodiment, the target protein of the invention is not fused to a reporter protein with enzymatic activity. In a particularly preferred embodiment, the target protein is not fused to GFP. Thus, alternatively viewed, it is preferred that any tag fused to the target protein is a non-protein tag.

For a tag to be fused to the target protein, it is generally transcribed and translated with the target protein as a single molecule. Thus, antibodies which bind to the target protein and which may be labelled with HRP etc are not considered to be fused to the target protein. In such cases, the target protein may be detected using the HRP tag since this is not part of a fusion molecule with the target protein.

Thus, tags can be attached to a target protein by expressing such proteins as fusion proteins. As such, short tags are preferred, to allow proteins of interest to maintain a native-like conformation. Further, C-terminal tags are preferred, although N-terminal His tags are also used. It will be appreciated that a detection step involving the use of a tag fused to a target protein can only be used where the target protein is derived from a recombinant expression system.

Therefore, generally this detection method will not be used when the target protein is for example obtained from a patient.

Target proteins (in methods employing a separation step) can further be detected via fusion tags which act as the substrate in enzymatic detection methods, His tags being particularly suitable in this regard. For example, INDIA His Probe-HRP (Pierre, Rockford Ill., USA) can be used for detection wherein the target protein is either poly-histidine tagged or is histidine rich and where the target protein is detected by Nickel activated derivative of horseradish peroxidase which binds to His tags. Target proteins may also be detected on the basis of their own enzymatic activity.

Detection may alternatively be based on affinity binding between the target protein and a detection moiety or between a tag fused to the target protein and a detection moiety, for example an antibody, antibody fragment or affibody (non Ab based protein binding partner) in methods employing a separation step. Preferably, target proteins may be detected using antibodies, monoclonal or polyclonal, either directed to a tag or directly to the target protein (expressed on its own or as a fusion). Antibodies which are directed to the target protein are typically used to detect a target protein from a patient sample. Such methods allow for rapid and reliable analysis of a wide variety of target proteins, including those which themselves possess no catalytic activity. Target protein can also be detected using semi quantitative mass spectrometry (MS). In a fourier transform ion cyclotron resonance experiment using an orbitrap instrument typically 1000-2000 proteins can be detected simultaneously in a sample from a lysate. In a preferred embodiment a temperature scan of cells followed by lysis, filtration and in a final step the detection of all remaining soluble protein using mass spectrometry, at each temperature of the scan, allows precipitation curves to be measured in parallel for many proteins. This global proteome melting curve analysis could for example be used to detect so called off target effects of drugs, i.e. to monitor which other proteins in the cell appear to bind the drug. This global proteome melting curve analysis could also be used when searching for drug targets for drugs or drug candidates for which the drug target is unknown. For example, compound library screening direct on cells can identify compounds that generate preferred phenotypes in these cells indicative that the compound effects processes in the cell that are useful as drug targets for a certain disease. However, it is normally very challenging to identify with which protein or proteins in the cell the drug candidate interact. The global proteome melting curve analysis for thermal shift changes allow this to be performed for the proteins which are available at sufficient level to be detectable with MS.

As discussed above, the present invention is also directed to a method which may not employ a separation step, but which involves an analysis step where a soluble or native target protein is detected using two or more affinity reagents which bind with higher affinity to the soluble or native form of the target protein than to the unfolded and/or insoluble form of the target protein. In this way, such affinity reagents can determine whether soluble or native forms of the target protein are present in a sample after heating and thus whether folded and potentially ligand bound target protein is present. The two or more affinity reagents must together be capable of distinguishing between soluble or native, and unfolded and/or insoluble forms of a target protein and thus must be capable of detecting soluble or native target protein against a background of unfolded and/or insoluble (precipitated) target protein and other proteins.

This form of the method of the invention is particularly advantageous as there is no specific requirement to carry out a separation step and particularly no separation step may be carried out. In this respect, the method of this embodiment involves minimal processing steps, which potentially allows automation of the method and an increased throughput, where large numbers of samples can be handled.

The "affinity reagent" as used herein thus refers to any reagent which is capable of binding with a higher affinity to a soluble or native form of a target protein than to an unfolded and/or insoluble form of the same target protein. An affinity reagent which binds with a higher affinity to a soluble or native form of a target protein compared to the unfolded and/or insoluble form of the target protein will have a smaller $K_D$ value for its association with the soluble or native target protein than for its association with the unfolded and/or insoluble form of the target protein. Particularly, an affinity reagent of the present application may have a $K_D$ value which is at least 100 times smaller with respect to binding to the soluble or native form of the target protein than the $K_D$ with respect to binding to the unfolded and/or insoluble form of the target protein. Methods for measuring the $K_D$ values of affinity reagents are well known in the art. Thus, the use of two or more affinity reagents (e.g. antibodies) for the detection of the soluble or native target protein allows the use of affinity reagents which may have a lower specificity for the soluble or native target protein than if a single affinity reagent (e.g. antibody) was used alone to detect the soluble or native target protein. As two or more affinity reagents (e.g. antibodies) are required to be bound to the soluble or native target protein to result in its detection, less specific affinity reagents can be used and can still result in a specific method of detecting the soluble or native target protein (and hence ligand bound target protein). Thus some binding of at least one of the affinity reagents (e.g. antibodies) may occur to the unfolded and/or insoluble form of the target protein, although binding to the soluble or native form of the target protein is preferential and association may be at least 100 times greater than association to the unfolded and/or insoluble form of the target protein. Similarly, each affinity reagent particularly binds with higher affinity to the soluble or native form of the target protein than to any other protein present in the sample.

In a particular embodiment, at least one of the affinity reagents (e.g. antibodies) used the method is capable of binding specifically to the soluble or native form of the target protein but not to the unfolded and/or insoluble form of the target protein (or to any other protein). Thus, the reagent may bind specifically to the soluble or native target protein and any binding to the unfolded and/or insoluble target protein may be non-specific and minimal. Thus, in this instance, one affinity reagent is capable of specific binding and one or more other affinity reagents may be capable of binding to the soluble or native form of the target protein with higher affinity than to the unfolded and/or insoluble form of the target protein. Further, the method provides for the use of two or more affinity reagents which bind specifically to the soluble or native form of the target protein but not to the unfolded and/or insoluble form of the target protein.

In order to distinguish soluble (or native) from unfolded and/or insoluble target protein, the affinity reagent may recognize (particularly specifically recognize) an epitope or sequence of the target protein which is exposed in the soluble or native form of the protein but not in the unfolded and/or insoluble form of the protein. The two or more affinity reagents recognise different epitopes or sequences on the target protein and thus provide a more specific method of distinguishing soluble or native from unfolded and/or insoluble target protein, than when identifying a single epitope or sequence. (Although with proteins which are homodimers, the affinity reagents may be directed to the same epitope). Thus, both (or more) affinity reagents must be bound to the target protein in order to determine that a soluble or native form of the target protein is present. A positive detection of soluble or native target protein (and thus ligand bound target protein) is only achieved if both (or more) affinity reagents (e.g. antibodies) are bound.

The affinity reagent may be an antibody, antibody fragment, affibody, peptide, aptamer, DARTs or other small molecule that binds to the soluble or native form of a target protein with a higher affinity than to the unfolded and/or insoluble form of the target protein. Particularly, at least one affinity reagent is an antibody and more particularly two antibodies are used in the method. The invention however also encompasses the use of different affinity reagents e.g. the use of an antibody and another affinity reagent.

The detection of the two or more affinity reagents (particularly two antibodies) may be using a reporter assay which results in a signal change when the two or more affinity reagents are bound to soluble or native protein. Generally, the two or more affinity reagents are labeled (particularly with different labels) and the close proximity of those labels to one another when bound via the affinity reagents to the soluble or native form of the target protein results in a change in signal e.g. the emission of fluorescence or the production of light or fluorescence at a different wavelength (to the labels when used alone) or the quenching of fluorescence. Such reporter assays are often referred to as proximity reporter assays, e.g. a FRET (fluorescence resonance energy transfer) based method (or a variant thereof, such as BRET (Bioluminescence Resonance Energy Transfer)) may be used in the present method for detection, where the close association of one label (a donor molecule) attached to an affinity reagent, to a second label (an acceptor molecule) attached to an affinity reagent, results in the production or alteration of a signal. Thus, the presence of the two or more labels bound to the soluble or native protein via the affinity reagents results in a detectable signal change. In one embodiment e.g. FRET, transfer of energy from the donor to the acceptor molecule labels may result in the emission of fluorescence by the acceptor molecule. In this way, the labeling of two (or more) affinity reagents (antibodies) which bind to the soluble form of a target protein, with labels which have a signal change when in close proximity to each other, can result in the emission of fluorescence when both are bound to the soluble target protein, thus enabling detection of the soluble target protein. Donor and acceptor molecules used in FRET/BRET based methods are well known in the art and include pairs such as cyan fluorescent protein and yellow fluorescent protein (both variants of green fluorescent protein); and bioluminescent luciferase and YFP. Such a method requires the binding of both (or more) affinity reagents (e.g. antibodies) to the soluble target protein before detection of any signal (e.g. luminescence) is achieved. In this aspect, one affinity reagent may be labeled with donor molecule and the second affinity reagent may be labeled with the acceptor molecule.

In a particular embodiment, the labels which demonstrate a signal change when in close proximity (e.g. when bound via affinity reagents to the soluble target protein),e.g. donor and acceptor molecules, may be coated or comprised within separate bead populations which may then be used to bind to each affinity reagent (antibody). Thus, the beads coated with one of the labels (e.g. the donor molecule) may be used attached to the first affinity reagent e.g. antibody and the beads coated with the second label (e.g. the acceptor molecule) may be used to detect the second affinity reagent (e.g. antibody). Each bead population (e.g. donor or acceptor) may be conjugated with a further reagent to allow binding to either the first or second affinity reagent (e.g. antibodies). For example, a bead population (donor or acceptor) may be streptavidin coated to allow binding to biotinylated affinity reagent (e.g. antibody) or may be conjugated to protein A to allow binding to an antibody affinity reagent. Methods of attaching beads to affinity reagents such as antibodies are well known in the art.

It will be appreciated that the two or more affinity reagents (e.g. antibodies) may be labeled (e.g. with donor or acceptor molecules) prior to addition to the sample or after addition to the sample. However, particularly, the affinity reagents (antibodies) may be labeled before addition to the sample. The AlphaScreen Surefire assay format (Perkin Elmer) may be particularly used in the method of the invention, where other antibodies may be attached to the beads provided (see Osmond et al., Analytical biochemistry, 403, 94-9101, 2010, incorporated herein by reference).

Other methods for detection of the bound affinity reagents include proximity ligation assays (such as Duolink from Olink) and ELISAs.

Methods for producing affinity reagents, such as antibodies which may bind to the soluble form of a target protein but not the insoluble form of a target protein are known in the art. For example, the study of the 3D structure of a soluble and insoluble protein can enable determination of epitopes which are exposed on the soluble form but not the insoluble form. Antibodies or peptides which bind to such epitopes can then be produced using standard methods.

Further, methods are known which can be used to identify antibody pairs that bind to a target protein e.g. methods employing surface plasmon resonace biosensors or ELISA. Further, Bembenek et al. (Analytical Biochemistry, 408, 2011, 321-327, incorporated herein by reference), reported a bead based screening method using antibody capture on Protein A Alphascreen beads to analyse and select pairs of antibodies capable of binding to the same target.

As discussed above, this aspect of the invention relates to a method where no separation step is specifically required to be performed and detection of target protein-ligand interaction via the detection of soluble target protein can be carried out on cellular samples potentially without a lysis step. Thus, in this way, ligand interaction with a target protein can be assessed by immunohistochemistry of tissues e.g. by 2D immunohistochemistry of tissues. Such a method and use of the method in this way provides a previously unavailable insight into interactions which are actually occurring in particular cells. Thus, the method can also in principle be used for mapping ligand binding in histological sections. For example, if a histological sample from a drug treated patient is exposed to a constant temperature which is selected so the target protein gives a strong signal due to ligand binding, this sample can subsequently be frozen and sectioned and attributed to an immunoassay detecting the remain folded or soluble proteins. More soluble proteins will be present in the regions of this histological section where the effective ligand concentration is higher. In this way one can, for example, map which region of a sample, e.g. a tumour, the drug has penetrated.

Molecule/ligand binding to target proteins can be investigated in a recombinant expression system. Thus, genes/cDNAs/coding regions for the target protein can be transformed or transfected into expression systems in vectors/ constructs, such as plasmids, viral vectors, cosmids and YACS. Such vectors may contain regulatory sequences and other elements well known in the art. For example, the gene/cDNA/coding region may be placed under the control of a promoter in a vector. Promoters used are generally capable of expressing the target protein within a particular host. In a specific embodiment, the promoter used is inducible i.e. the expression of the target protein can be controlled. Such inducible promoters/systems include lac wherein induction of expression is controlled by the addition of IPTG and tet on/off, wherein the induction of expression is controlled by the presence/absence of tetracycline and others are known in the field.

As described previously, the method of the invention may be used to screen libraries of small molecules for those which will bind to a target protein. In a preferred embodiment, this is carried out using multi-well plates where each compound of the library is added to an aliquot of cells, or a cell lysate. Alternatively libraries of mutant target protein may be screened to determine a mutant target protein which shows altered binding to a particular ligand. For example, mutant target proteins can be identified which have a closer or tighter association with a ligand than wildtype target protein. Where mutant target proteins are being assessed, measurements of the stability of the protein without ligand are desirable to decide whether the stabilisation is due to the ligand interaction or due to the mutant itself being more stable i.e. the mutation having a stabilising effect on the mutant protein. If the ligand is another protein, the stability measurement could instead be carried out on this nonmutant protein, where mutated protein variant can be selected which stabilises the non-mutated protein. This could, for example, be used to mature binding proteins (i.e. the ligands) such as, for example, antibodies, FAB-fragments, single chain antibodies or affibodies where random mutations are added to the binding protein and variants with apparent improved binding are detected by measuring improved stabilization of the non-mutated protein. In such a way, higher affinity binders could be selected from lower affinity binders. When binding proteins can serve as protein drugs targeted against e.g. specific receptors or cytokines, the method could be used to improve the affinity of such binders to the drug target of the protein drug.

Many different methods of mutagenesis are known in the art which could be employed to create a variant of the target protein or a library of variants of target protein. Possible procedures include truncation of the sequence, use of an exonuclease enzyme, introduction of a randomized site mutations using e.g. error prone PCR, introduction of randomised cassette or site-directed mutagenesis. For truncations, the number of nucleotides removed may be less than 2000, preferably less than 1000 and more preferably less than 800. Introduction of a randomised cassette for mutagenesis preferably uses a cassette containing less than 100 nucleotides.

Mutagenesis may be carried out on several copies of a nucleic acid sequence encoding the target protein so that a set of different mutated sequences can be screened, hence increasing the probability of identifying a target protein variant with the desired ligand binding properties. The use of random mutagenesis is especially preferred where there is no prior knowledge of which particular mutations may yield a variant which for example binds to the ligand more tightly i.e. has a higher affinity for the ligand.

Libraries of proteins can be created where the coding region has been randomly mutagenised and where different length constructs have been generated by erase-a-base or random priming reactions.

Thus, the methods of the present invention can be used to detect target protein variants which have altered and preferably have increased or higher affinity binding to a ligand. Additionally, the methods of the invention can be used to determine whether a target protein in a cell culture or patient sample will interact with a particular test molecule e.g. a drug. Hence, a preferred use of the method is to determine drug-protein interactions in cell culture during the drug development cycle to confirm that the drug binds to the target protein in this cell type. Similarly the method can be used to monitor drug binding to non-desired proteins, so called off-target binding. Another preferred use of the method is to determine drug-protein interactions in patient samples (e.g. tissue, blood, lymph etc), to provide an indication as to whether a particular drug therapy will be effective for that patient. If a tissue sample is to be examined, then the method of the invention may also incorporate a step of extracting a target protein from the tissue. Additionally or alternatively, a step of lysis may be used. Appropriate lysis conditions are described above Once a target protein and ligand interaction has been detected in a non-purified sample using the method of the invention, it may be desirable to identify the sequence or structure of the target protein, particularly if target protein variants have been investigated. Alternatively, as discussed above, the results obtained may be used to determine whether a drug therapy is likely to be effective in a patient and thus to tailor the therapy provided to a patient.

The binding of a high affinity drug to an established drug target, as shown in e.g. Examples 4, 5, 6 and 7, typically leads to a stabilisation of the target protein as supported by the positive shift of the melting temperature to a higher temperature. However, there are also ligands that, upon binding to the target protein, cause a negative shift of the melting temperature to a lower temperature, i.e. destabilisation. For example, negative shifts can be seen for ligands which form covalent-type bonds (including some metals) to a target protein. It is presumed that the binding energy of a covalent bond, and the energetically unfavourable strains generated by forming such a bond, could, in some cases, promote the destabilisation of a protein. For example, Ericsson et al. (Anal Biochem 357 (2006) pp 289-298) show that compounds which contain heavy metal atoms, such as lutetium (III) chloride hexahydrate, are able to destabilise a number of bacterial proteins upon binding.

Thus, in a further aspect, the invention provides a method of determining whether a non-purified sample contains a target protein bound to a ligand of interest, wherein said ligand is not a fusion protein, comprising the steps of:

a) exposing said non-purified sample to a temperature which is capable of causing or enhancing precipitation of the target protein bound to said ligand to a greater extent than it is capable of causing or enhancing precipitation of the unbound target protein;

b) processing the product of step a) in order to separate soluble from insoluble protein; and c) analysing either or both the soluble and insoluble protein fractions of step b) for the presence of target protein, wherein said target protein is not detected on the basis of enzymatic activity of a tag, peptide, polypeptide or protein fused thereto.

Another further aspect of the invention provides a method of determining whether a non-purified sample contains a target protein bound to a ligand of interest comprising the steps of:

a) exposing said non-purified sample to a temperature which is capable of causing or enhancing precipitation of the target protein bound to said ligand to a greater extent than it is capable of causing or enhancing precipitation of the unbound target protein;

b) processing the product of step a) in order to separate soluble from insoluble protein; and c) analysing the soluble protein fraction of step b) for the presence of target protein, wherein said target protein is not detected on the basis of enzymatic activity of a tag, peptide, polypeptide or protein fused thereto.

In the above aspects, one would expose the non-purified sample to a temperature capable of causing or enhancing precipitation of the target protein bound to ligand, because the target protein bound to the destabilising ligand would precipitate at a lower temperature compared to the unbound target protein. Therefore, at the distinguishing temperature described in step a), one would expect to find more of the bound protein in the insoluble protein fraction, and more of the unbound protein in the soluble protein fraction.

Discussions of the various features of the methods of the invention and preferred embodiments set out in relation to stabilisation caused by ligand binding apply, *mutatis mutandis*, to these aspects of the invention where ligand binding causes destabilisation.

In some instances, there might be a physiological substrate or co-factor, such as ATP or NADP, present in a cell lysate, which binds to the target protein even before the ligand is added to the sample. When a ligand of interest is added to such a lysate, the shift of the melting curve towards higher temperatures will typically be smaller, as compared to the case when no physiological ligand is present in the lysate. In an extreme case, a very low affinity ligand (typically giving small positive thermal shifts) such as an early drug lead candidate, could at very high concentrations compete out a stronger physiological ligand (typically giving large positive thermal shifts) such as NADP. The replacement of the physiological ligand could, in such a case, lead to a negative shift, i.e. a shift to a lower melting temperature, when the apparent shift is the difference between the shifts of the two ligand bound forms of the protein. Under such circumstances, because the negative shift would be detectable as a decrease in the melting temperature of the target protein, the aspects of the invention relating to the ligand causing destabilisation would apply here.

The invention further encompasses an instrument for use in the methods of the invention wherein said instrument comprises a heating means, a means for separating soluble from insoluble protein and a means for analysing protein for the presence of target protein, e.g. for analysing suitable protein.

Alternatively viewed, an instrument adapted in use to carry out the method of the invention comprising a heating means, a means for separating soluble from insoluble protein and a means for analysing (e.g. soluble) protein for the presence of target protein, is encompassed.

Further, the invention is directed to the use of an instrument comprising a heating means, a means for separating soluble from insoluble protein and a means for analysing (e.g. soluble) protein for the presence of target protein in the methods of the invention.

The instruments are arranged such that a sample is first contacted with the heating means, then separation means and finally analysing means.

The term "a heating means" as used herein refers to any heat source which is capable of heating a sample to a particular temperature. Thus, the heating means may consist or comprise of a hot plate which can be programmed to heat a sample to a particular temperature, e.g. a PCR machine can be used to heat a sample in this way. Further, a heating means could comprise an incubator or a water bath.

The term "a means for separating soluble from insoluble protein" refers to any known apparatus which is capable of separating soluble and insoluble protein. Thus the means may comprise a filter paper where soluble protein will pass through the filter paper. Alternatively, the means may comprise an apparatus which is capable of imparting a centrifugal force on the heated sample e.g. a centrifuge. Additionally, the means may comprise an apparatus which is capable of affinity capture of the soluble protein. Such an apparatus may comprise antibodies or other affinity reagents which are capable of recognising the folded structure of the soluble protein. Antibodies, metal conjugates or other affinity reagents may be linked to magnetic beads or column resin. Insoluble protein can be removed by washing.

The term "means for analysing (e.g. soluble) protein for the presence of target protein" as used herein refers to any apparatus which would be capable of detecting the target protein. Thus this could refer to a mass spectrometer but more preferably may refer to the apparatus required to e.g. detect an antibody labelled with HRP or a fluorescent molecule bound to the target protein (i.e. nitrocellulose membrane or a fluorimeter). Further, the means for analysing protein for the presence of target protein may comprise an affinity column for binding target protein. The means for analysing protein for the presence of target protein may further comprise any of the reagents necessary to detect the target protein, or alternatively, these may be provided separately. Finally, the present invention encompasses the use of a kit in the methods of the invention which comprises an antibody and/or a non-protein tag.

The invention will now be further described in the following non-limiting Examples in which:

FIG. 1 shows the assessment of the presence of soluble protein for three different proteins expressed in an *E. coli* sample after exposure to a range of different temperatures. The known melting temperatures of the purified proteins are shown on the right hand side of the figure.

FIG. 2 shows the assessment of the presence of soluble PIK3C3-protein after the addition of the ligands Wortmannin and 3-[4-(4-Morpholinyl)thieno[3,2-d]pyrimidin-2-yl]-phenol (Compound 15e) (+). Reference sample without added ligand are also shown (−). A thermal shift can be seen in the samples with ligands. The lanes with proteins plus ligand are more thermally stable than proteins without ligand.

FIGS. 3A-3B show the Western blot membranes of targets cyclin dependent kinase-2 (CDK-2) (FIG. 3A) and protein kinase C (PKC) (FIG. 3B). The dark bands indicate that the presence of soluble protein was detected up to a specific temperature and become fainter and ultimately disappear as the temperature is increased (from left to right). The pellet containing precipitated protein from the highest temperature was dissolved in loading buffer and loaded in the last lane of the gel in order to show the presence of the target protein in this fraction.

FIG. 4 shows the levels of soluble thymidylate synthase (TS), dihydrofolate reductase (DHFR), CDK-2 or PKC protein present after exposure to a range of different temperatures in mammalian cell extracts. The X axis represents the exposed temperature (° C.) and the Y axis represents the integrated intensity from the Western blots.

FIG. 5 shows the thermal melting curve from human cell extracts of soluble DHFR protein after the addition of the inhibitor methotrexate (♦). Reference sample without inhibitor is also shown (■). The X axis represents the exposed temperature (° C.) and the Y axis represents the integrated intensity from the Western blots.

FIG. 6 shows the thermal melting curve from human cell extracts of soluble TS protein after the addition of the inhibitor raltitrexed (+). Reference sample without inhibitor is also shown (•). The X axis represents the exposed temperature (° C.) and the Y axis represents the integrated intensity from the Western blots.

FIGS. 7A-7B show the thermal melting curve of soluble methionine-aminopeptidase-2 after the addition of the ligand TNP-470 (x) either from cow liver extract (FIG. 7A) or from human cell extract (FIG. 7B). Reference sample without ligand is also shown (○). The X axis represents the exposed temperature (° C.) and the Y axis represents the integrated intensity from the Western blots.

Figure 10:
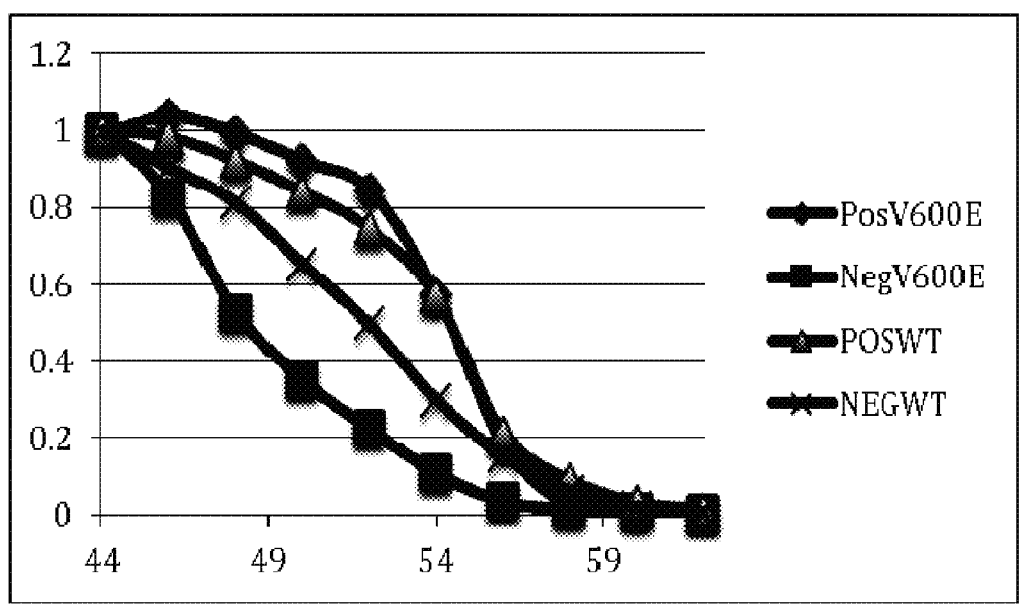

FIG. 10 shows the thermal melting curve of either soluble V600E variant B-raf protein (♦) or wild-type B-raf protein (▲) after the addition of the ligand SB590885. Reference samples without ligand are also shown, both for the V600E varient B-raf protein (■) and the wild-type B-raf protein (x). The X axis represents the exposed temperature (° C.) and the Y axis represents the integrated intensity from the Western blots.

Figure 11A:
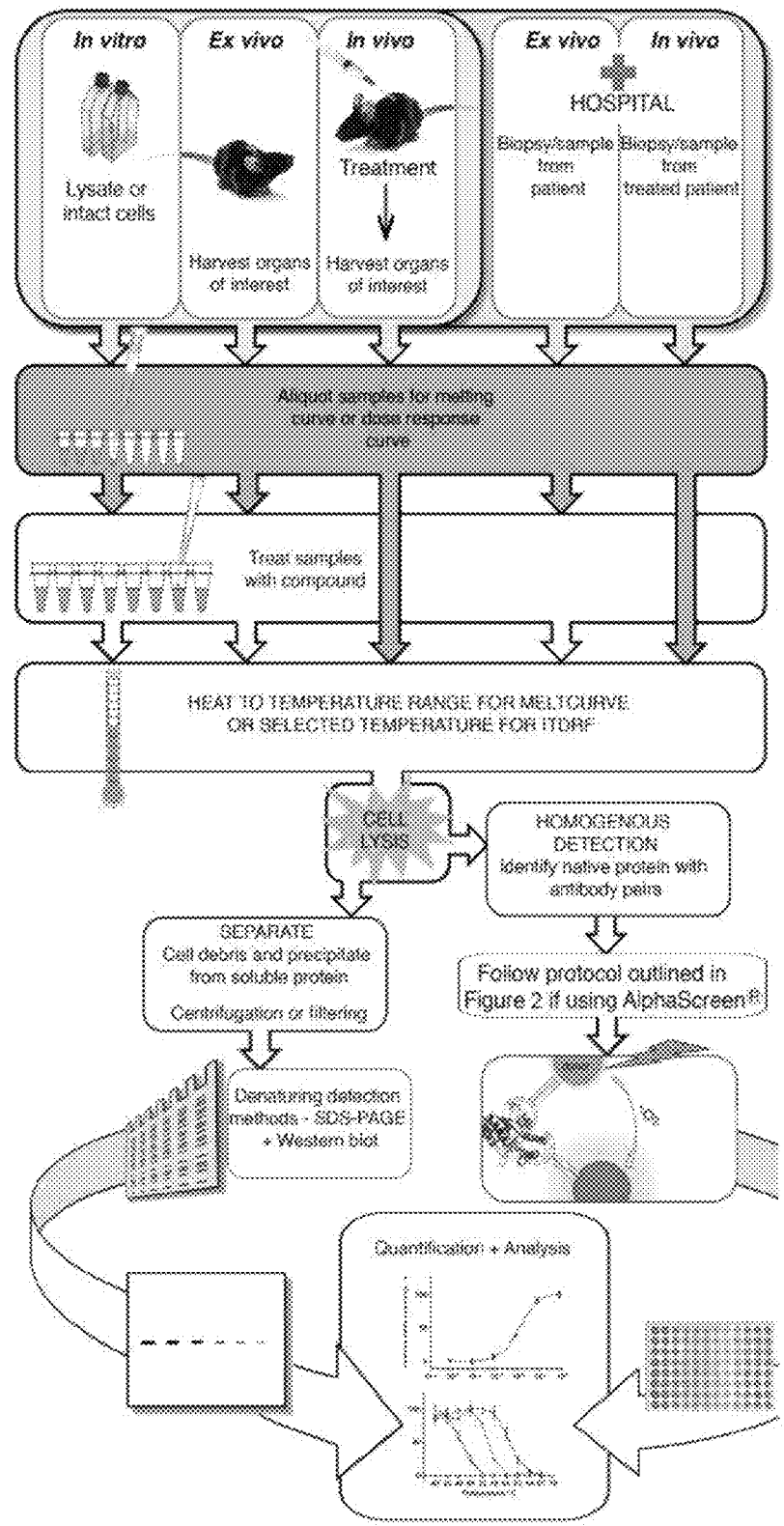

FIG. 11A shows a schematic illustration of CETSA (both a homogenous assay format and with a separation step), when using samples from different origins. Samples are aliquoted depending on the experiment to be performed (i.e. whether a CETSA melting curve is being established or whether hating to a selected temperature is being carried out) and when applicable, test compounds may be added at a high dose (melt curve) or at a series of different concentrations (for heating to a selected temperature). Samples are then heated over a temperature range or at a constant temperature (for dose response curve). After heating, the samples are homogenised and lysed. If Western blotting is used for detection, a separation step is carried out and or if Alphascreen (FRET) is used for detection, then separation is not necessary.

Figure 11B:
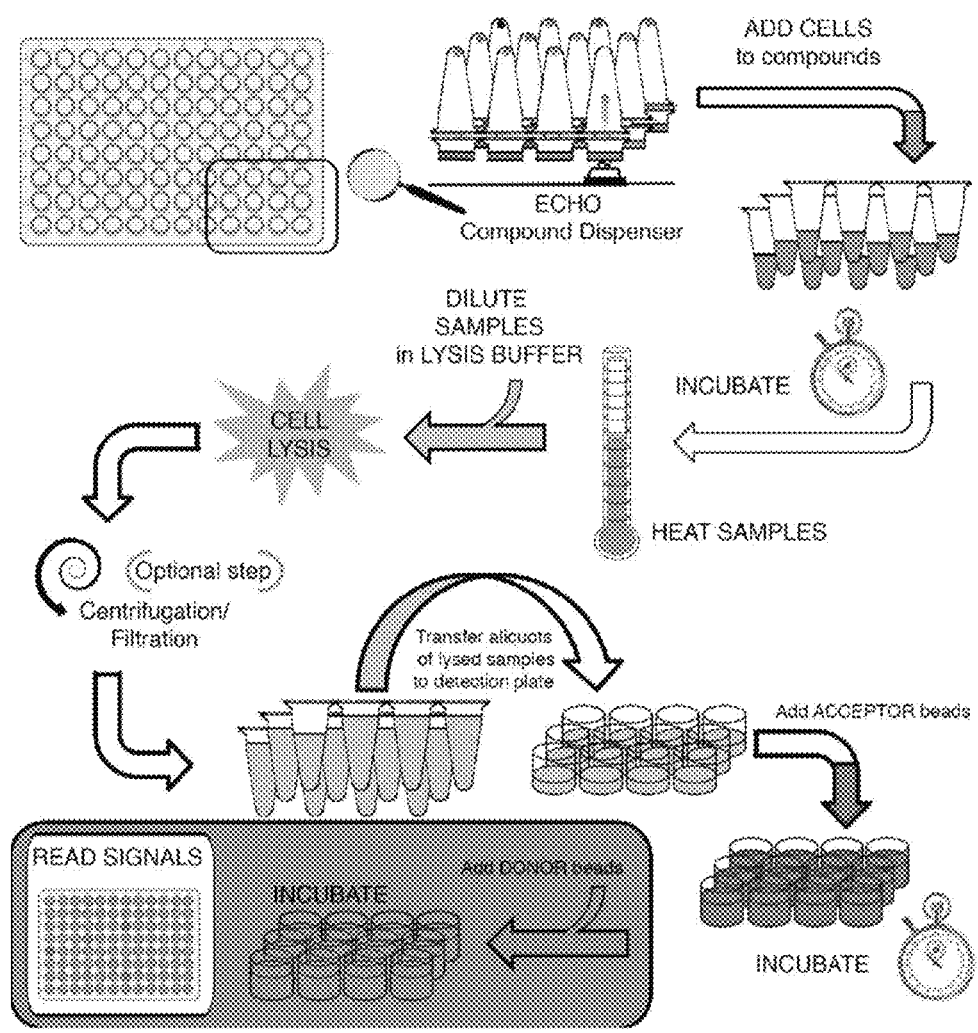

FIG. 11B shows a screen format assay where compound stock solutions are dispensed into wells and cell suspension is then added to the wells. A pre-incubation of samples for approximately 30 minutes is carried out before heating the microplates in a PCR machine at a defined temperature for approximately 3 minutes. The plate left to cool and then samples are diluted with lysis buffer. The cell debris and protein aggregates may be optionally removed by centrifugation/filtration. The diluted samples may be transferred to a detection plate (or not if the plate is already suitable) and detection is achieved by using a standard protocol for Alphascreen beads.

Figure 12A:
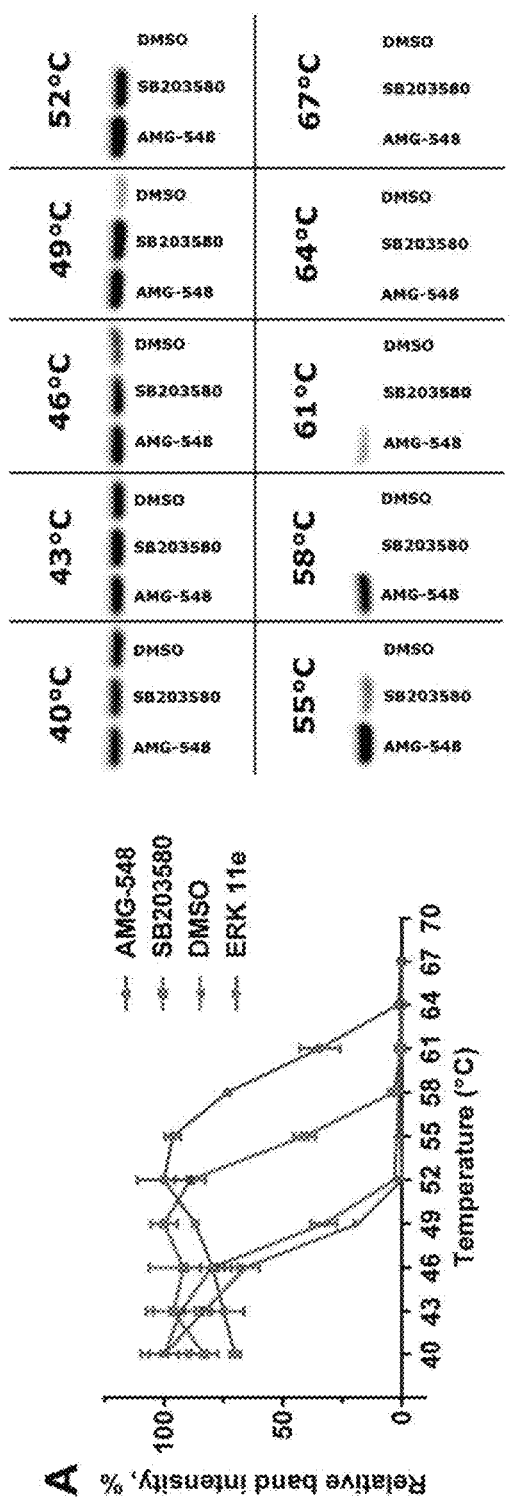
Figure 12B:
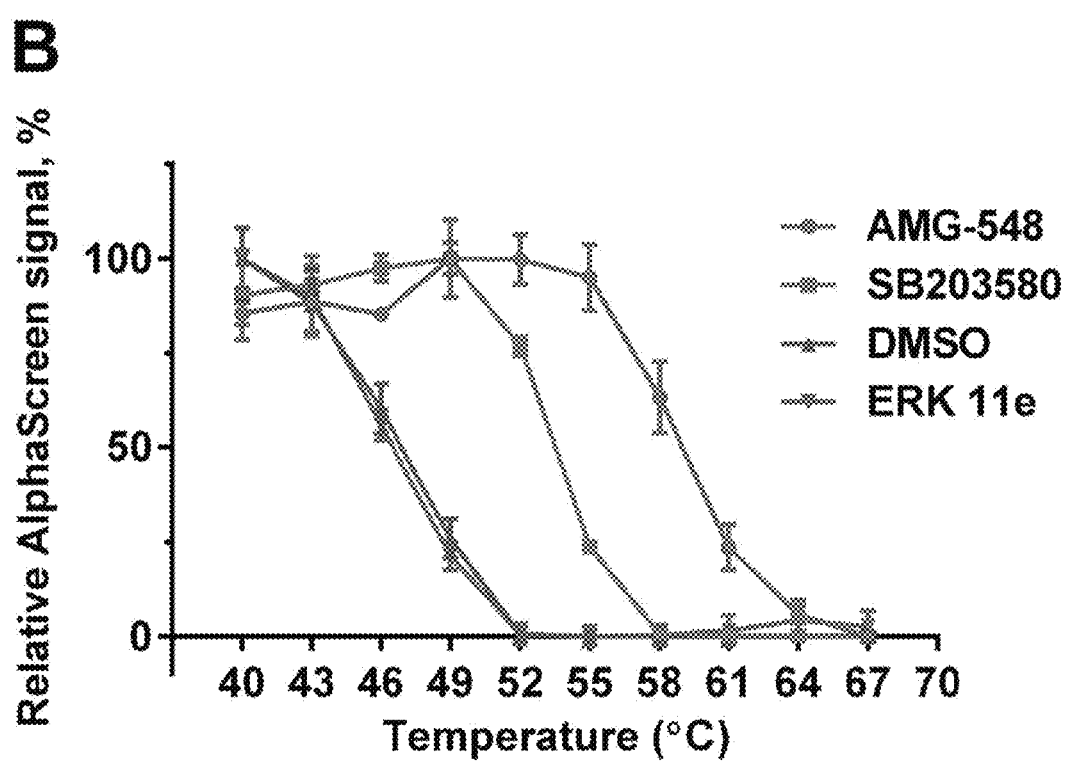

FIGS. 12A-12B show the remaining amount of p38α for detection by Western blot (FIG. 12A) and by the Surefire assay (FIG. 12B) (as a function of the temperature to which HL60 cells were heated). Measurements were taken in the absence of inhibitors (▲) and in the presence of several different compounds, including the dual Erk1/2 inhibitor ERK11e ( ) as a negative control and the established p38α inhibitors SB203580 (■) and AMG-548 (•) as positive controls. All experiments were performed at three independent occasions and data are given as the average and SEM from these experiments.

Figure 13A:
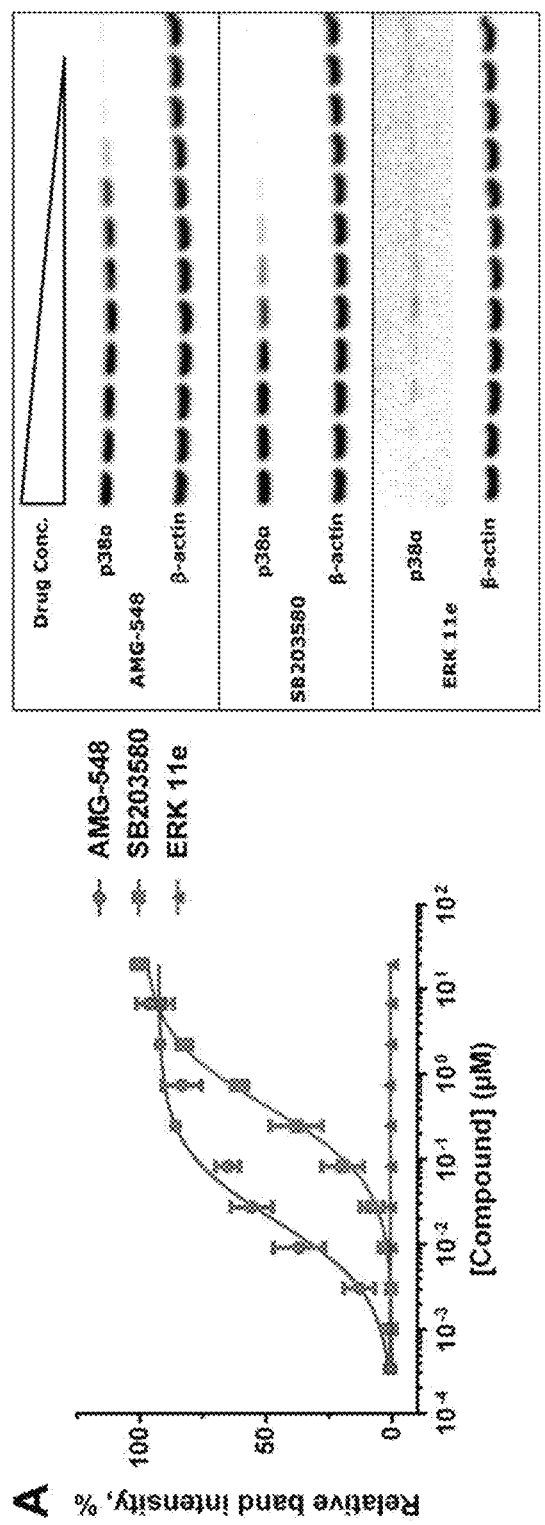
Figure 13B:
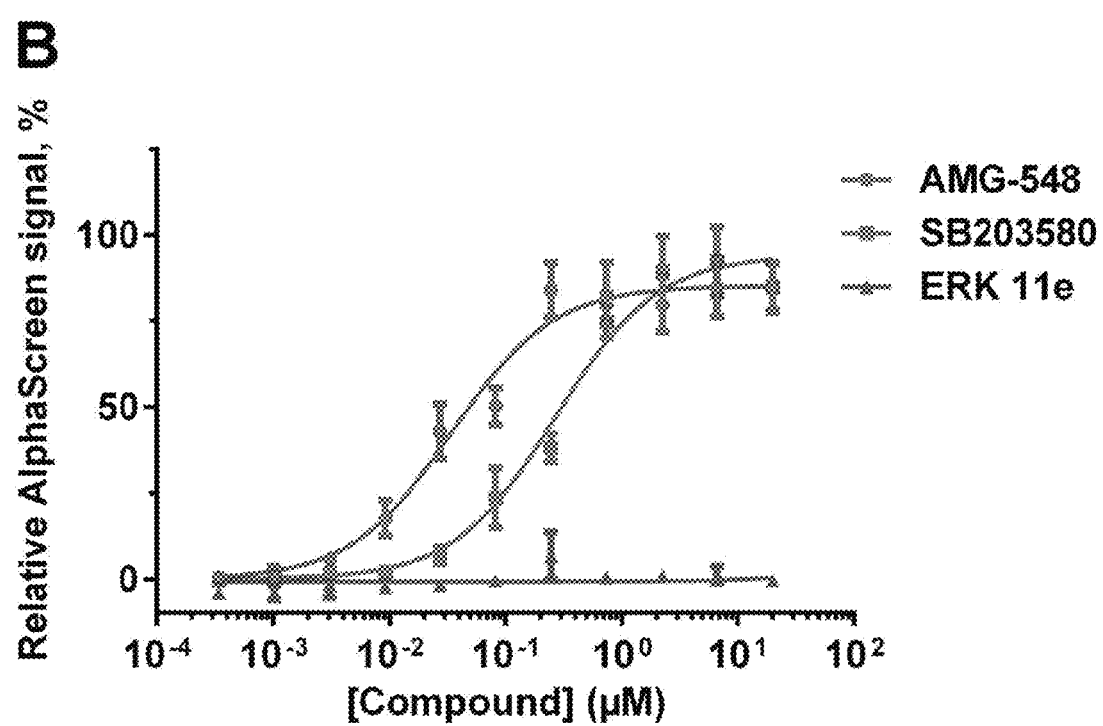

FIGS. 13A-13B show an illustration of the amount of p38α accessible for detection using western blot (FIG. 13A, left panel; the right panel shows raw Western blot data for p38α as well as corresponding β actin levels) and the SureFire assay (FIG. 13B) directed towards p38α as a result of the stabilisation observed in the presence of increasing concentrations of compounds in HL-60 cells. Data were obtained in the presence of the dual Erk1/2 inhibitor ERK 11e 9) as a negative control and the established p38α inhibitors SB203580 (■) and AMG-548 (•) as positive controls. All experiments were performed at three independent occasions and data are given as the averages and SEM from these experiments. The data sets were fitted with a hyperbolic model.

FIG. 14A shows heat maps with raw data from the AlphaScreen based reading following heating of HL60 cells at 50° C. for three minutes. The experiment was performed in two 96-well plates in the presence of 50 μM (top) and 10 μM (bottom) of compound from a diversity set, with three of the original compound solutions replaced with AMG-548 (well E9), SB203580 (well D2) and ERK (well G06).

Figure 14B:
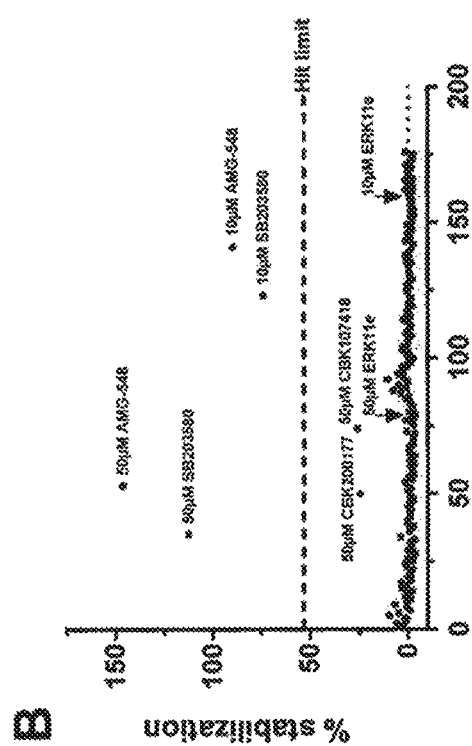

FIG. 14B shows a scatter plot of the screening data after conversion to a % stabilisation based on the negative and positive controls on each plate. The first 96 points are derived from the 50 μM plates (running from A1, A2, etc through to H12), whereas the following 96 points are derived from the 10 μM plate.

EXAMPLE 1

Determination of Melting Temperatures of Four Test Proteins

Three human soluble protein expression constructs in an expression vector with an N-terminal His-tag were used in order to determine the melting temperature of each protein in the cell. This was done by exposing the protein-containing cell to a panel of increasing temperatures and after each temperature step spotting the cells onto a "lysis/filtration sandwich" soaked in lysis buffer. By using this lysis/filtration step, the soluble protein (up to the protein's specific melting temperature) could be detected on a capturing nitrocellulose membrane as dark spots, whereas precipitated protein (i.e., above its specific melting temperature) was not able to pass through the filter membrane and could therefore not be detected.

Materials and Methods

Liquid cultures of *E. coli* cells overexpressing the three proteins of interest were started by inoculating 1 ml Luria-Bertani broth (LB) (Formedium Ltd., UK) containing 50 μg/mlkanamycin (Sigma-Aldrich Co., USA) and 35 μg/ml chloramphenicol (Duchefa Biochemie, The Netherlands) with frozen *E. coli* from glycerol stocks in a 96-well deep-well plate (Porvair Plc., UK). The cultures were incubated on a shaking board overnight at 700 rpm and +37° C. The following day 100 μl of each overnight culture was transferred to a corresponding well of a new 96-well deep-well plate containing 900 µl LB, 50 µg/ml kanamycin, and 35 µg/ml chloramphenicol. The cultures were incubated on a shaking board at 700 rpm and +37° C. After 1.5 hours the temperature was lowered to +18° C. (30 min.), and protein expression was induced by adding 100 mM IPTG (Anatrace/Affymetrix Co., USA). The cells were grown overnight on a shaking board at 700 rpm and +18° C. The cells were pelleted by centrifugation the following day at 1500 g for 2 min. and 900 µl supernatant was removed from each well by aspiration and discarded. The cell pellets were resuspended in the remaining 100 µl of medium (i.e., concentrated 10-fold). The cell suspensions were transferred to 8-tube PCR strips (Applied Biosystems, UK) and placed in a thermocycler. The following temperature program was used: +27° C.-+75° C. with 3° C. increments and a 3 min. hold at each step. After the 3 min. hold at each temperature the thermocycler was paused, and 2 µl of each cell suspension was quickly spotted onto a "lysis/filtration sandwich" consisting of Durapore filter membrane with 0.45 µm pore size (Millipore Inc., USA) (top layer), Protran BA 45 nitrocellulose membrane (Schleicher & Schuell, Germany) (middle layer), and 3MM Whatman paper (VWR Int'l. Ltd., UK). The "lysis/filtration sandwich" was soaked in native lysis buffer (20 mM Tris-HCl pH 8.0, 100 mM NaCl, 10 mg/ml Lysozyme (Sigma-Aldrich Co., USA), 25 U/µl Benzonase nuclease (Novagen, Denmark) and Complete protease inhibitor EDTA-free tablet (Roche, Switzerland). After spotting the cells onto the "lysis/filtration sandwich", the abovementioned procedure was repeated at each temperature step. After spotting the last cell aliquot the "lysis/filtration sandwich" was incubated for 15 min. at room temperature in order to allow complete lysis and liquid cellular material transfer through the filter membrane. The "lysis/filtration sandwich" was thereafter frozen at −80° C. for 10 min. and then thawed for 10 min. at +37° C. This freeze/thaw procedure was repeated 3 times. The nitrocellulose membrane was blocked in TBST buffer (20 mM Tris-HCl pH 7.5, 500 mM NaCl, 0.05% Tween-20) containing 1% BSA (VWR Intl. Ltd., UK) for 1 hour. The blot was then washed 3 times for 10 min. in TBST with some agitation (tabletop shaker). The membrane was incubated for 1 hour with INDIA HisProbe-HRP (Thermo Scientific, USA) diluted 1:5000 in TBST. The blot was then washed 3 times for 10 min. in TBST. Chemiluminescent detection of target protein expression level in each spot on the blot was performed using SuperSignal West Dura (Pierce) Extended Duration Substrate (Thermo Scientific, USA). Chemiluminescence was detected and recorded using a CCD camera (BioRad Laboratories, Inc., USA).

Results

Figure 1:
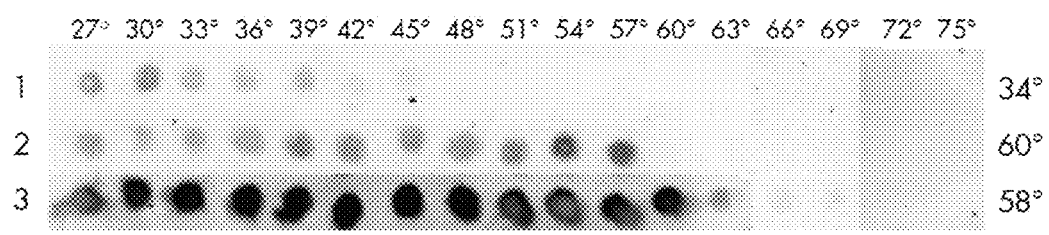

The dark spots indicating the presence of soluble protein were detected up to a specific temperature; they became fainter and ultimately disappeared at higher temperatures (FIG. 1). A comparison with previous data on the melting temperatures of the three IMAC-purified proteins (right panel) showed good correlation between the two sets of results. The melting points are not expected to be exact as the proteins have different solvent environment in a cell and in a purification buffer. This experiment shows that these proteins have distinct melting points in the cellular environment and that these melting points can be easily detected by monitoring the precipitation of the protein.

EXAMPLE 2

Detection of an Increase of Melting Temperature after Binding to a Ligand

An expression construct of human soluble PIK3C3 protein in an expression vector with N-terminal His-tag was used to investigate a possible increase in melting temperature of the PIK3C3 construct after addition and binding of either of two PIK3C3 specific inhibitors; Wortmannin and Compound 15e. After treatment with or without one of the two inhibitors the cells expressing the PIK3C3 constructs were exposed to a panel of increasing temperatures and after each temperature step the cells expressing the proteins were spotted onto a "lysis/filtration sandwich" soaked in lysis buffer. By using this lysis/filtration step on the "lysis/filtration sandwich" the soluble protein (up to the construct's specific melting temperature) could be detected on a capturing nitrocellulose membrane as dark spots, whereas precipitated protein (i.e., above its specific melting temperature) was not able to pass through the filter membrane and could therefore not be detected. Melting temperatures of constructs treated with Compound 15e or Wortmannin were compared with those of untreated samples.

Materials and Methods

Liquid cultures of E. coli cells overexpressing PIK3C3 constructs were started by inoculating 1 ml Luria-Bertani broth (LB) (Formedium Ltd., UK) containing 50 µg/ml kanamycin (Sigma-Aldrich Co., USA) and 35 µg/ml chloramphenicol (Duchefa Biochemie, The Netherlands) with frozen E. coli from glycerol stocks in a 96-well deep-well plate (Porvair Plc., UK). The cultures were incubated on a shaking board overnight at 700 rpm and +37° C. The following day 100 µl of each overnight culture was transferred to a corresponding well of a new 96-well deep-well plate containing 900 µl LB, 50 µg/ml kanamycin, and 35 µg/ml chloramphenicol. The cultures were incubated on a shaking board at 700 rpm and +37° C. After 1.5 hours the temperature was lowered to +18° C. (30 min.), and protein expression was induced by adding 100 mM IPTG (Anatrace/Affymetrix Co., USA). The cells were grown overnight on a shaking board at 700 rpm and +18° C. The cells were pelleted by centrifugation the following day at 1500 g for 2 min. and 900 µl supernatant was removed from each well by aspiration and discarded. The cell pellets were resuspended in the remaining 100 µl of medium (i.e., concentrated 10-fold). For each of the experiments 1 mM of the PIK3C3 inhibitor Compound 15e (Santa Cruz Biotechnology, Inc., USA) or 500 µM Wortmannin (Santa Cruz Biotechnology, Inc., USA) dissolved in DMSO (Sigma-Aldrich Co., USA) or the equivalent volume (1 µl and 0.5 µl respectively) of pure DMSO was added and the samples were gently agitated for 30 min. at room temperature. The cell suspensions were transferred to 8-tube PCR strips (Applied Biosystems, UK) and placed in a thermocycler. The following temperature program was used: +27° C.-+75° C. with 3° C. increments and a 3 min. hold at each step. After the 3 min. hold at each temperature the thermocycler was paused, and 2 µl of each cell suspension was quickly spotted onto a "lysis/filtration sandwich" consisting of Durapore filter membrane with 0.45 µm pore size (Millipore Inc., USA) (top layer), Protran BA 45 nitrocellulose membrane (Schleicher & Schuell, Germany) (middle layer), and 3MM Whatman paper (VWR Int'l. Ltd., UK). The "lysis/filtration sandwich" was soaked in native lysis buffer (20 mM Tris-HCl pH 8.0, 100 mM NaCl, 10 mg/ml Lysozyme (Sigma-Aldrich Co., USA), 25 U/µl Benzonase nuclease (Novagen, Denmark) and Complete protease inhibitor EDTA-free tablet (Roche, Switzerland). After spotting the cells onto the "lysis/filtration sandwich", the abovementioned procedure was repeated at each temperature step. After spotting the last cell aliquot the "lysis/filtration sandwich" was incubated for 15 min. at room temperature in order to allow complete lysis and liquid cellular material transfer through the filter membrane. The "lysis/filtration sandwich" was thereafter frozen at −80° C. for 10 min. and then thawed for 10 min. at +37° C. This freeze/thaw procedure was repeated 3 times. The nitrocellulose membrane was blocked in TBST buffer (20 mM Tris-HCl pH 7.5, 500 mM NaCl, 0.05% Tween-20) containing 1% BSA (VWR Int'l. Ltd., UK) for 1 hour. The blot was then washed 3 times for 10 min. in TBST with some agitation (tabletop shaker). The membrane was incubated for 1 hour with INDIA HisProbe-HRP (Thermo Scientific, USA) diluted 1:5000 in TBST. The blot was then washed 3 times for 10 min. in TBST. Chemiluminescent detection of target protein expression level in each spot on the blot was performed using SuperSignal West Dura (Pierce) Extended Duration Substrate (Thermo Scientific, USA). Chemiluminescence was detected and recorded using a CCD camera (BioRad Laboratories, Inc., USA).

Results

Figure 2:
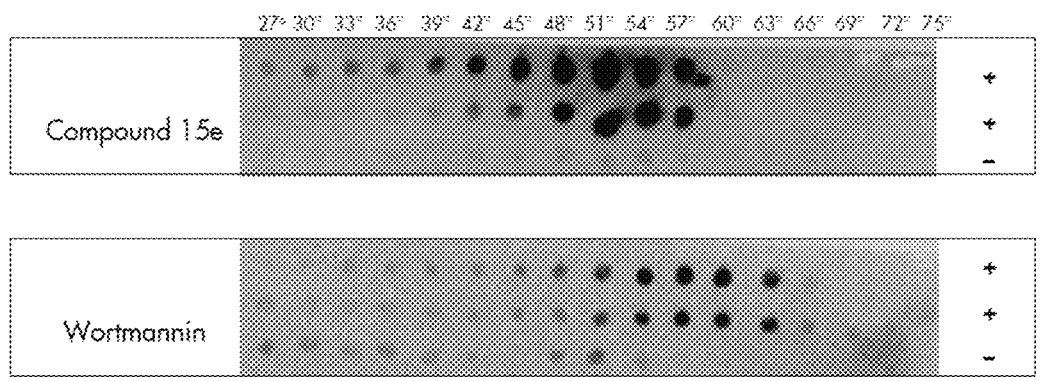

The dark spots indicating the presence of soluble protein were detected up to a specific temperature beyond which they where no longer visible (FIG. 2). Addition of Compound 15e resulted in an increased melting temperature from ca +55° to +58° C. whereas addition of Wortmannin resulted in an increased melting temperature between ca +55° and +65° C. A comparison with previous data on the melting temperatures of IMAC-purified PIK3C3 construct with and without the addition of Compound 15e or Wortmannin showed good correlation between the two sets of results. This experiment shows that it is possible to detect an increase in melting temperature of the PIK3C3 construct in the cellular environment after addition and binding of either of two PIK3C3 inhibitors Wortmannin and Compound 15e.

EXAMPLE 3

Determination of Melting Temperature of Four Test Proteins in Mammalian Cell Systems In order to determine the melting temperature of four proteins, lysate was prepared from cultured mammalian cells and exposed to a panel of increasing temperatures. After the temperature steps, precipitated protein was removed, leaving only soluble protein (i.e. up to the protein's specific melting temperature) to be detected.

Materials and Methods

Lysate was prepared from cultured human adenocarcinoma cells (A549). Cells were disrupted on ice in hypotonic buffer and with homogenisation. The suspensions were freeze-thawed multiple times and all insoluble aggregates and cell debris were pelleted by centrifugation after completed lysis. The supernatant containing optically clear cytosolic fraction was aliquoted into 8-strip PCR tubes and subject to a panel of increasing temperatures. After heating for three minutes, the samples were cooled and precipitated protein was pelleted by centrifugation. The supernatant, containing soluble protein, was loaded on separating gels. In addition, the pellet containing precipitated protein from the highest temperature was dissolved in loading buffer and loaded in the last lane of the gel in order to show the presence of the protein in this fraction. The gels were blotted onto a Western blot nitrocellulose membrane. The membrane was washed and blocked with blocking reagent and probed with primary against dihydrofolate reductase (DHFR), thymidylate synthase (TS), cyclin dependent kinase-2 (CDK-2) and Protein Kinase C (PKC). Secondary antibodies were bound, and the signal from the bound secondary antibody was detected by chemiluminescense and recorded with a CCD camera. The intensities were measured and plotted.

Results

Figure 3A:
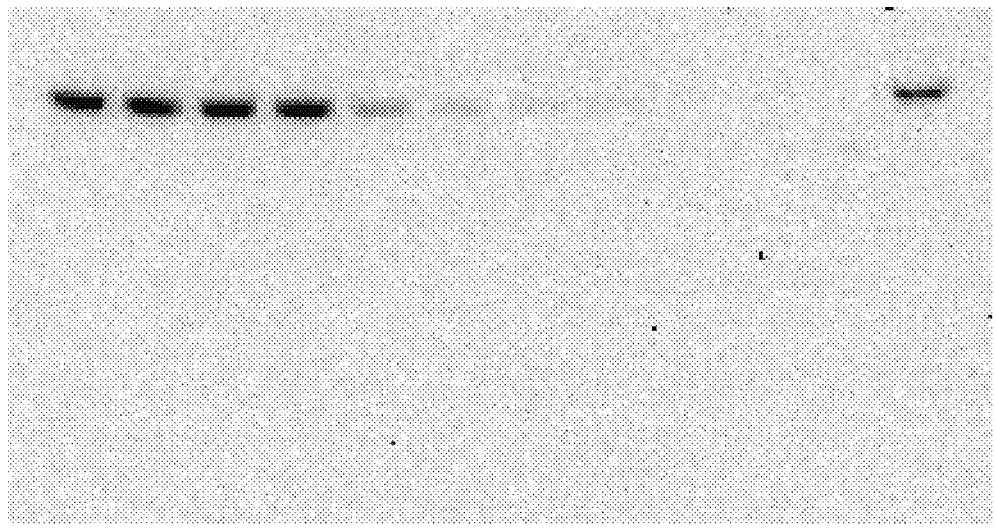
Figure 3B:
Figure 4:
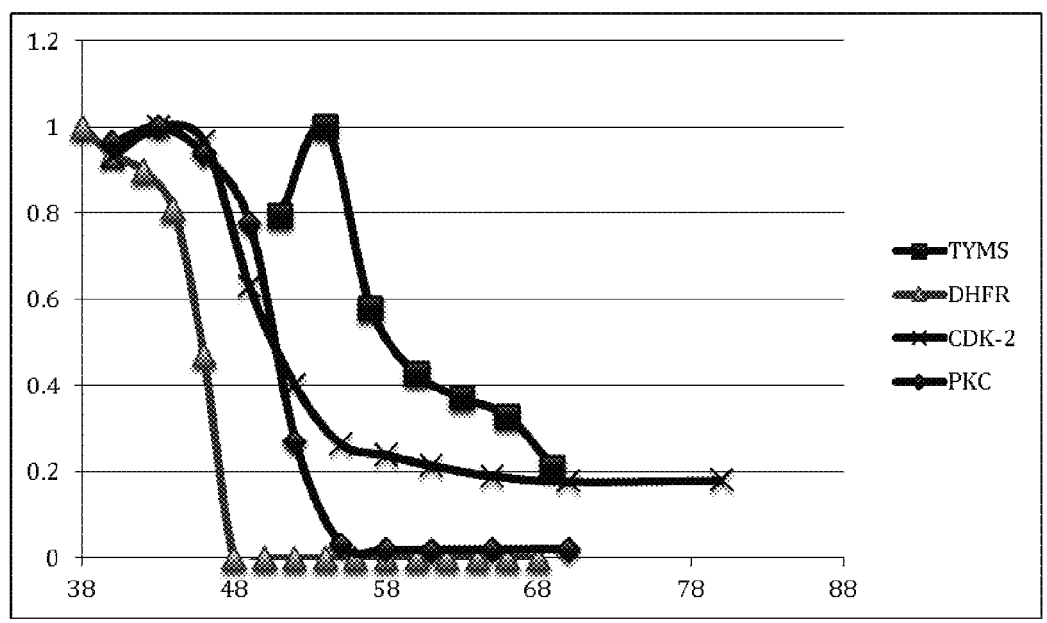

The dark bands indicating the presence of soluble protein were detected up to a specific temperature; they became fainter and ultimately disappeared at higher temperatures (FIG. 3). This experiment shows that these proteins have a distinct melting temperature and behaviour in the cellular environment and that these melting points can easily be detected by monitoring the precipitation of the protein (FIG. 4).

EXAMPLE 4

Detection of an Increase of Melting Temperature after Binding to a Ligand in Mammalian Cells In order to investigate the possible increase or decrease in melting temperature after addition and binding of inhibitors, the proteins dihydrofolate reductase (DHFR) and thymidylate synthase (TS) were studied in cultured mammalian cells.

Lysate from cultured adenocarcinoma cells were treated with one of two inhibitors; raltitrexed or methotrexate, where the possible stabilising or destabilising effects of methotrexate was analysed for DHFR and raltitrexed was analysed for TS. After treatment with or without the inhibitors the samples were subjected to a heating step followed by removal of precipitated protein. The melting temperatures of treated samples were compared to those of untreated samples.

Materials and Methods

Lysate was prepared from cultured human adenocarcinoma cells (A549). Cells were disrupted on ice in hypotonic buffer and with homogenisation. The suspensions were freeze-thawed multiple times and all insoluble aggregates and cell debris were pelleted by centrifugation after completed lysis. The supernatant containing optically clear cytosolic fraction was divided into four aliquots, two were supplemented with their respective ligand with one corresponding negative control. The concentration of added ligand was 10 times the described IC50 value for the drug/target interaction. Each ligand was dissolved in DMSO and the final concentration was set to 1%.

After incubation, each aliquot was divided into 8-tube PCR strips and subjected to an array of temperatures ranging from +36° C. to 60° C. for DHFR and +51° C. to +69° C. for TS (guided by the melt curve from Example 3). After heating for three minutes, precipitated protein was pelleted by centrifugation. The resulting supernatants were loaded on a separating gel and transferred to a Western blot nitrocellulose membrane. After blocking of the membrane, it was probed with primary and secondary antibodies. The signal from the bound secondary antibody was detected by chemiluminescense and recorded with a CCD camera. The intensities were plotted to visualize the changes in melting temperature following ligand treatment.

Results

Figure 5:
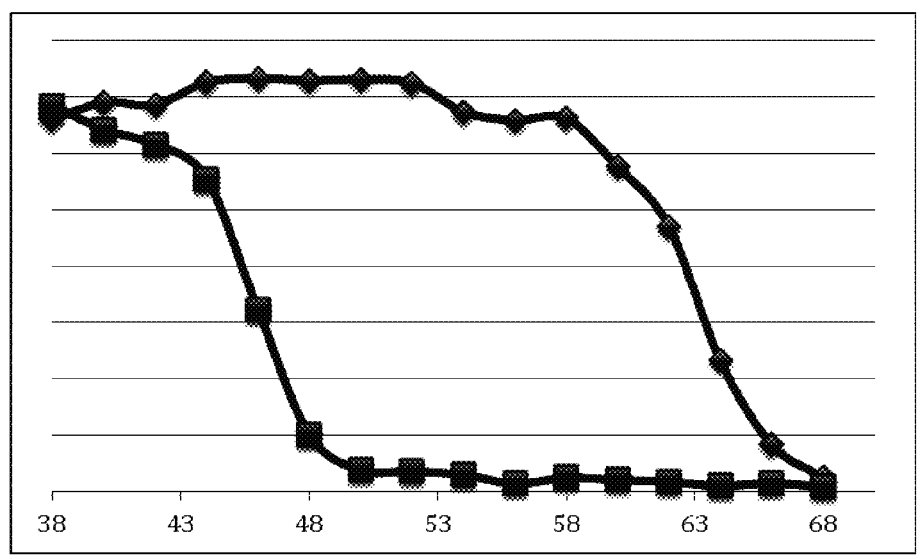
Figure 6:
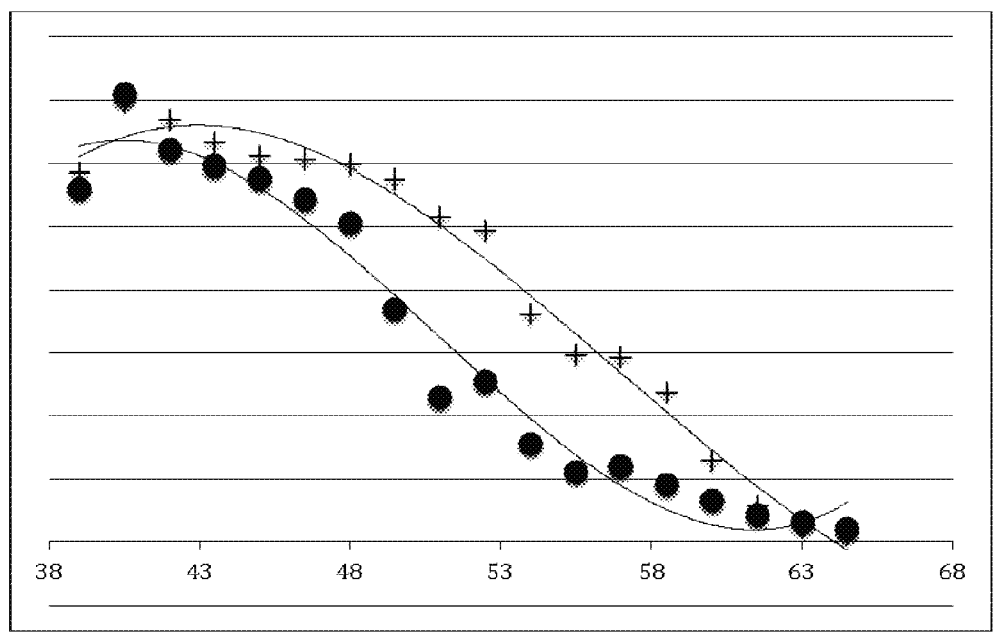

Addition of methotrexate or raltitrexed resulted in an increased melting temperature (FIGS. 5 and 6). This experiment shows that it is possible to detect an increase in melting temperature of DHFR or TS in the cellular environment after the addition and binding of the respective inhibitors methotrexate and raltitrexed.

EXAMPLE 5

Cellular Thermal Shift Studied in Different Cell Systems and Organisms to Determine Changes in Melting Temperature Upon Binding of a Ligand In order to study the effects of ligand binding in different systems, the possible stabilising or destabilising effects upon addition of the ligand TNP-470, an antiangiogenic agent, to the protein methionine-aminopeptidase-2, was determined. Studies were done on cells from two different systems: a) intact cow liver biopsies incubated with TNP-470 and b) human cultured cells incubated with TNP-470. All samples were compared to reference samples, which had not been exposed to TNP-470. After treatment with or without the inhibitor, the samples were prepared and subjected to an array of increasing temperatures. The precipitated protein fraction was pelleted by means of centrifugation and the supernatant from each temperature step was analysed on gels and by Western blot. Melting temperatures of proteins treated with TNP-470 were compared to those of untreated samples.

Materials and Methods

Lysate was prepared for cultured human cells (K562) and cow liver samples by disruption on ice in hypotonic buffer and with homogenisation. The suspensions were freeze-thawed multiple times and all insoluble aggregates and cell debris were pelleted by centrifugation after completed lysis. The lysate of each cell type was divided into two aliquots, where one was supplemented with TNP-470 (dissolved in pure DMSO) and the other with an equivalent volume of pure DMSO. After incubation at room temperature the samples were divided into fractions of 50 microliters in 8-tube PCR strips and subsequently placed in a Veriti thermocycler.

Next, a series of temperatures were applied to different samples ranging between +56° C. to +88° C. with 2 or 4° C. increments and a 3 minute hold at each step. Following heating, the samples were cooled and the precipitated protein pelleted by centrifugation. 20 microliters of each supernatant was removed, supplemented with gel loading buffer and fully denatured by heating. The samples were loaded on a separating gel, which after full run time was blotted onto a nitrocellulose membrane. The membrane was washed and blocked with blocking reagent and probed with primary and secondary antibodies. The signal from the bound secondary antibody was detected by chemiluminescense and recorded with a CCD camera. The intensities were plotted to visualize the changes in melting temperature following ligand treatment.

Results

Figure 7A:
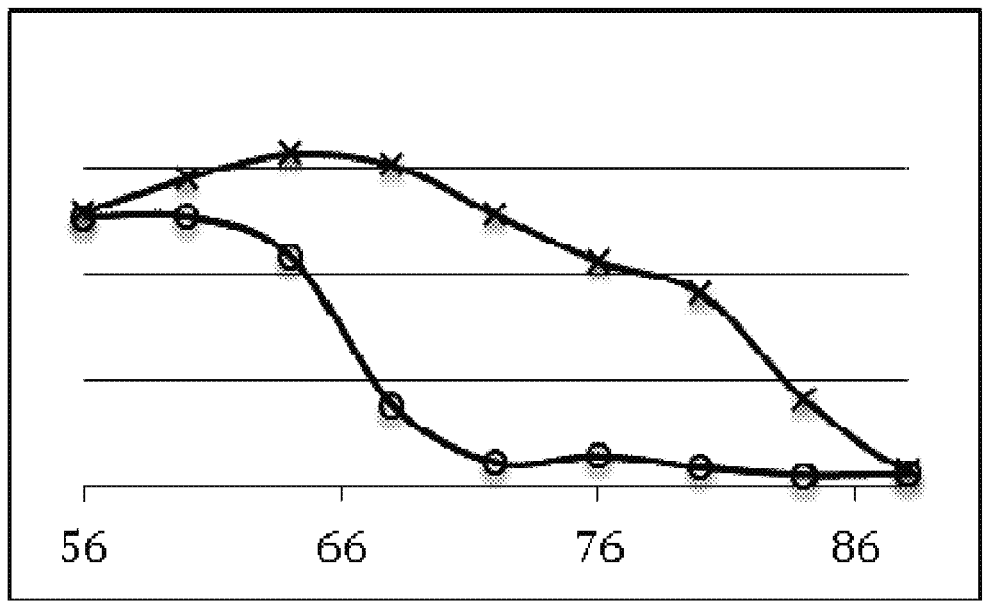
Figure 7B:
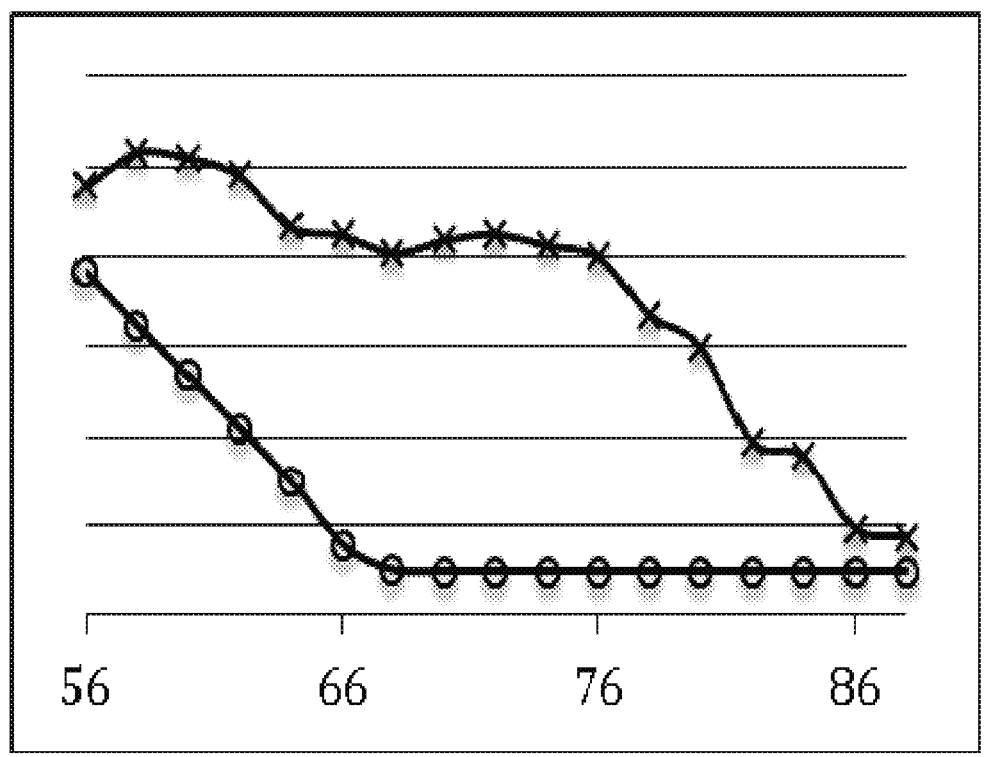

Dark bands on the Western blot membrane indicates the presence of soluble protein still in the supernatant. The soluble protein was detected up to a specific temperature beyond which they were no longer visible. Addition of TNP-470 resulted in a shift in melting temperature for human cell lysate from 62° C. to 80° C. (an 18° C. shift) and for cow liver lysate from 66° C. to 80° C. (a 14° shift) (FIG. 7).

EXAMPLE 6

Dose Response Curve from the Concentration Dependence of the Thermal Stabilization For the purpose of constructing a dose-response curve to estimate apparent binding constants, cow liver lysate was subjected to a dilution series of ligand TNP-470, specifically targeting methionine aminopeptidase-2. Prior to this Example, curves corresponding to treated and untreated samples have been obtained (see Example 5) where the dose has been set at saturating levels. The differences in melting temperature can then be used to decide on a temperature where a treated sample is still present whilst an untreated sample will be precipitated. For this Example the temperature was set to +76° C. The dilution series was constructed as a series of 10-fold dilutions. The generated curve gives an indication of the concentration of the ligand needed to engage the target protein in the lysate.

Materials and Methods

Lysate was prepared from cow liver samples. Cells were disrupted on ice in hypotonic buffer and with homogenisation. The suspensions were freeze-thawed multiple times and all insoluble aggregates and cell debris were pelleted by centrifugation after completed lysis. The supernatant containing optically clear cytosolic fraction was aliquoted into 8-strip PCR tubes where each tube contained an increasing amount of the ligand TNP-470 so that the concentration of ligand ranged between 1 picomolar and 100 nanomolar and with the DMSO concentration at 1% of the final volume. The samples were incubated and subsequently heated to 76° C. for 3 minutes. Following heat treatment the samples were cooled and the precipitated fraction was pelleted by centrifugation. 20 microliter of each supernatant was removed and supplemented with gel loading buffer and fully denatured by heating. The samples were loaded on a separating gel, which after full run time was blotted onto a nitrocellulose membrane. The membrane was washed and blocked with blocking reagent and probed with primary and secondary antibodies. The signal from the bound secondary antibody was detected by chemiluminescense and recorded with a CCD camera. The intensities were measured and plotted.

Results

Figure 8:
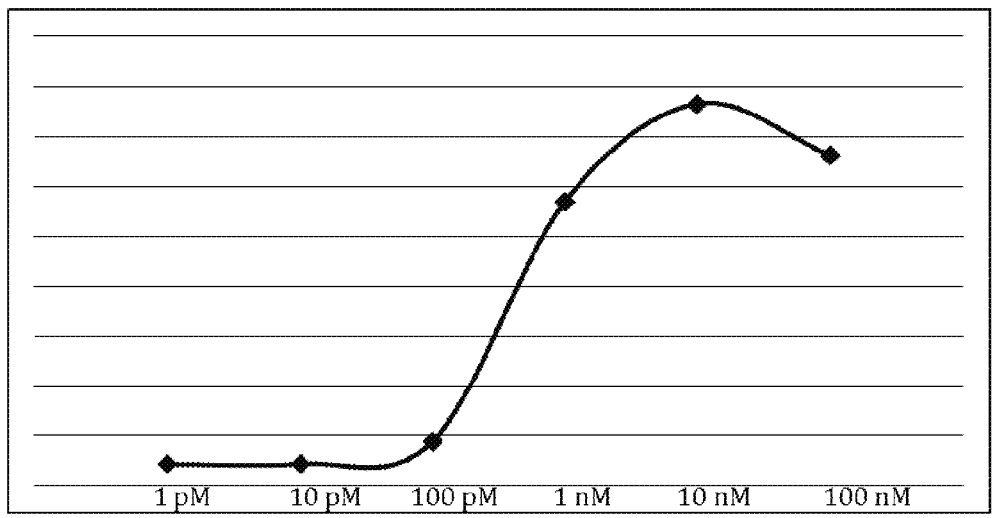
FIG. 8 shows the dose response curve of TNP-470 treatment of cow liver extract. The X axis represents the concentration of TNP-470 added and the Y axis represents the integrated intensity from the Western blots.

Dark bands on the Western blot membrane indicates presence of protein in the supernatant. If no or very little protein is present, no or very low signal will be visible. As the concentration of ligand increases, the amount of stabilised protein also increases. This is observed as a gradually increasing signal of the dark band on the Western blot membrane. Plotting the integrated intensities will render a dose-response curve (FIG. 8), which makes it possible to pinpoint an apparent concentration where half of the protein in the sample will have been engaged by a bound ligand (i.e. stabilised). This can have useful applications to set dosing regimes for patients or to find a therapeutic window for a drug by studies of apparent binding constants in different organs of the body.

EXAMPLE 7

Biosensor Application—Measurement of Presence of a Ligand in Complex Fluids

The presence of a ligand (e.g. a drug) for which there is a cognate ligand binding protein (e.g. a drug target) can be indicated even in complex test samples lacking the target protein. This is achieved by adding an aliquot of a sample containing the protein (e.g. lysate of the target cell or a purified protein) to the biological fluid test sample. In line with Example 6, a dose response curve can also be constructed using serial dilutions of a biological fluid (e.g. blood plasma or serum) containing the ligand of interest. The curve thus created can be fitted on to a dose-response curve generated by spiking to give an estimated concentration of the ligand in the biological fluid.

Materials and Methods

Lysate was prepared from cultured human adenocarcinoma cells (A549). Cells were disrupted on ice in hypotonic buffer and with homogenisation. The suspensions were freeze-thawed multiple times and all insoluble aggregates and cell debris were pelleted by centrifugation after completed lysis. The supernatant containing optically clear cytosolic fraction was aliquoted into 8-strip PCR tubes where each tube contained an increasing amount of the ligand TNP-470 dissolved in heat treated A549 lysate (heat treatment at 76° C. precipitated all target protein (methionine aminopeptidase-2) and ensured that no ligand would be consumed). As in Example 6, the concentrations ranged between 1 picomolar and 100 nanomolar effective concentration.

The samples were incubated and subsequently heated to 76° C. for 3 minutes. Following heat treatment the samples were cooled and the precipitated fraction was pelleted by centrifugation. 20 microliter of each supernatant was removed and supplemented with gel loading buffer and fully denatured by heating. The samples were loaded on a separating gel, which after full run time was blotted onto a nitrocellulose membrane. The membrane was washed and blocked with blocking reagent and probed with primary and secondary antibodies. The signal from the bound secondary antibody was detected by chemiluminescense and recorded with a CCD camera. The intensities were measured and plotted.

Results

Figure 9:
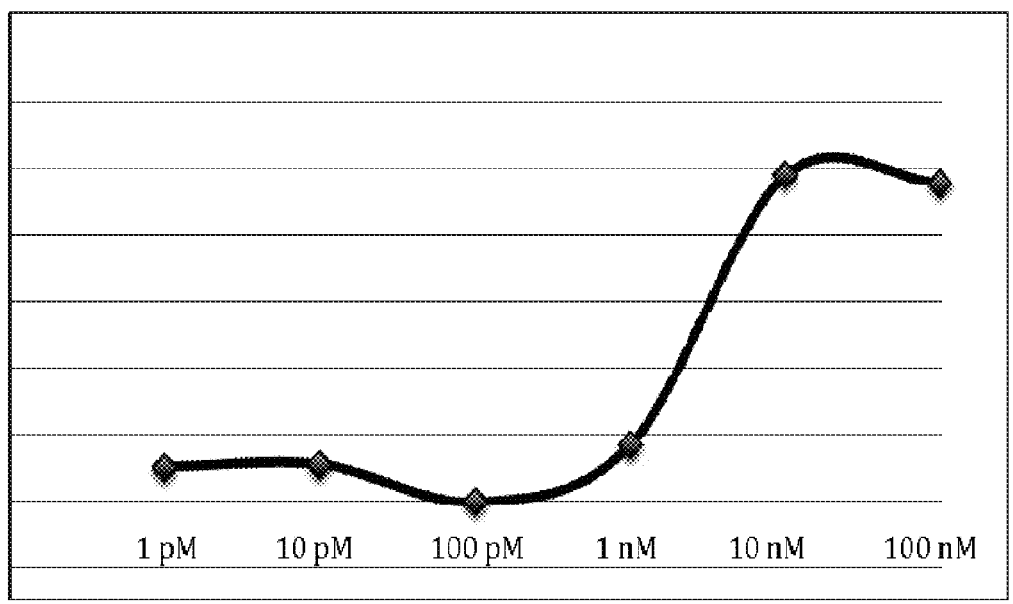
FIG. 9 shows the dose response curve of TNP-470 created by spiking with cell lysate containing target protein. The X axis represents the concentration of TNP-470 added and the Y axis represents the integrated intensity from the Western blots.

The heat-treated lysate was generated to mimic a biological fluid deficient in target protein. The spiking of the heat-treated lysate with ligand and the serial dilution thereof then produced a response curve (FIG. 9) that could be compared to and fitted on to an in vitro generated dose-response curve to get an estimate of how much ligand is present in the sample.

EXAMPLE 8

Ligands Targeting Specific Protein Variants

Within a human population, proteins exist as different variants, usually with a small number of amino acid substitutions. In some instances these substitutions promote diseases, such as, for example, cancer. The protein B-raf is involved in pathways where disturbances in regulation or function can cause such diseases. Many different amino acid substitutions have been described for B-raf that result in an oncogenic protein. Amino acid substitutions can also make a protein less capable of binding drugs, which is one driving cause behind resistance development during cancer treatment.

The ligand SB590885 is known to bind the V600E variant of B-raf, which can be hard to treat with medication such as Sorafenib. In this Example, we show that there is a difference in stability in the substituted versus the wild type protein and that the binding of ligand affects the protein variants to a different extent.

Materials and Methods

Lysate was prepared from cultured human A375 cells containing the V600E substitution in B-raf and K562, containing the wild type version thereof. Cells were disrupted on ice in hypotonic buffer and with homogenisation. The suspensions were freeze-thawed multiple times and all insoluble aggregates and cell debris were pelleted by centrifugation after completed lysis. The supernatants containing optically clear cytosolic fraction were each aliquoted into two tubes where each tube contained either the ligand SB590885 dissolved in DMSO or pure DMSO for control. The samples were incubated and subsequently aliquoted into 8-tube PCR strips in fractions of 50 microliters. A series of temperatures were applied to the different samples ranging between +44° C. to +62° C. with 2° C. increments and a 3 minute hold at each temperature. Following heating, the samples were cooled and the precipitated protein pelleted by centrifugation. 20 microliter of each supernatant was removed and supplemented with gel loading buffer and fully denatured by heating. The samples were loaded on a separating gel, which after full run time was blotted onto a nitrocellulose membrane. The membrane was washed and blocked with blocking reagent and probed with primary and secondary antibodies. The signal from the bound secondary antibody was detected by chemiluminescense and recorded with a CCD camera. The intensities were normalized and plotted to visualize the changes in melting temperature following ligand treatment (FIG. 10).

Results

The melting curves in FIG. 10 show that substituted V600E B-raf is less stable than wild type if no stabilising ligand is present. Upon treatment, V600E substituted B-raf is stabilised with approximately a 6° C. increase in the melting temperature, while the wild type protein once stabilised only showed a 3° C. increase in the melting temperature. After stabilisation, both the V600E B-raf and the wild-type B-raf showed a melting temperature of 55° C.

EXAMPLE 9

CETSA Using a Homogenous Assay Format

The thermal shift assay method can be used to detect ligand binding to a target protein in an assay where a separation step is excluded, by using a detection step which employs the use of two antibodies which are capable of binding to the soluble form of the target protein but not to the insoluble form of the target protein. Thus, after heating the sample (and optionally lysing the sample), detection of soluble target protein can be carried out using two antibodies which specifically detect the soluble target protein i.e. the folded form of the target protein.

The homogenous assay format using dual antibody detection of the soluble target protein (without performance of a separation step) allows the processing of more data points than carrying out the assay using traditional detection methods such as Western blotting. Such an assay further potentially allows the transfer of all steps to a microtiter plate (or similar format), which means that sample and reagent additions can be carried out by automated equipment. Heating and cooling can also be carried out using microtiter plate equipment. Thus, to optimise throughput, the number of assay steps must be brought down to a minimum. The method shown below hence allows the quantification of stabilized protein against a background of the same protein in a denatured and aggregated form, as well as cell lysate. The method below describes the use of antibodies (although other affinity reagents can be used) which recognize the folded structure, (AlphaScreen). The description below hence focuses on a high-throughput screening-amenable CETSA protocol that is based on a completely homogeneous assay without any wash or sample workup steps. This assay procedure is outlined in FIG. 11B.

There are a number of issues of importance when developing a microtiter-based CETSA protocol as well as considerations regarding the choice of protein source. It is good screening practice to reduce the overall assay variability and cost by minimizing sample transfers between plates. Homogeneous compound access to all material in the respective wells should also be ensured, and the precautions taken to achieve this may differ depending on whether the assay is performed in adherent or suspension cells, or tissue homogenates or cell lysates. As shown in FIG. 11B, it may be advantageous to add a large volume of a homogeneous cell suspension to a smaller volume of compound solution, as this facilitates mixing. During the incubation with compounds (preincubation), the microplate can optionally be shaken if required. The example case is based on the use of an incubation time of 30 min and a cell suspension.

This may be used for most systems, but in some cases adherent cell lines may require a solid support e.g. to retain target expression.

The microtiter plate may then be transferred to a PCR machine for carefully controlled heating. For isothermal experiments, the heating block only requires a single temperature, whereas when producing a melting curve a heating block with separate heating zones should be used, enabling for example, at least six temperatures to be assayed on each plate. Matched cooling blocks can be used to ensure consistent cooling rates between wells after heating.

In some cases complete cell lysis is important after heating, (complete cell lysis will prevent cell lysis variability between wells). Lysis can be carried out by freeze-thaw cycles, however, detergent-mediated cell lysis procedures are faster and more compatible with high-throughput formats.

The remaining stabilized and soluble protein must be detected against the background of denatured and aggregated proteins and cell debris in the homogeneous assay. The nature of the unfolded proteins in the intracellular aggregates is largely unknown, and may vary between proteins. An optional centrifugation or filtration separation step can be included to facilitate the detection of soluble material.

This example uses the AlphaScreen technology using a commercial SureFire kit against the protein kinase p38α. The SureFire assays are based on antibody pairs that recognize two different epitopes such that highly selective recognition of the protein target is achieved after binding of the antibodies to a protein A-conjugated acceptor bead and a streptavidin-coated donor bead, respectively. Approaches for efficient selection of suitable antibody pairs that can be applied when expanding the CETSA toolbox to other targets have been published.

Materials
Reagents

Liquid nitrogen (use any local provider), PBS, pH ~7.4 (Sigma-Aldrich, cat. no. P4417), TBS-Tween tablets (TBST; Calbiochem, cat. no. 524753), Kinase buffer (10×; Cell Signaling, cat. no. 9802), DMSO (99.9%; Sigma-Aldrich, cat. no. D8418), AMG-548 (Tocris, cat. no. 3920), SB203580 (Tocris, cat. no. 1202), ERK 11e (VX-11e; Tocris, cat. no. 4465), Nonfat dry milk powder (Semper), cOmplete, EDTA-free protease inhibitors (Roche, cat. no. 05056489001), HL-60 cell line (ATCC, cat. no. CCL-240), RPMI-1640 medium (Sigma-Aldrich, cat. no. R8758), Antibiotic-antimycotic solution (100×; Life Technologies, cat. no. 15240-062), FBS (Life Technologies, cat. no. 10500-064), 1-Glutamine (100×; Sigma-Aldrich, cat. no. G7513), Trypan blue (0.4% (wt/vol); Bio-Rad, cat. no. 145-0021), NuPAGE LDS sample buffer (4×; Life Technologies, cat. no. NP0007), NuPAGE reducing agent (10×; Life Technologies, cat. no. NP0009), SeeBlue Plus2 prestained protein molecular weight standard (Life Technologies, cat. no. LC5925), NuPAGE Novex 4-12% (wt/vol) bis-Tris midi gels, 26 well (Life Technologies, cat. no. WG1403BOX), NuPAGE MES SDS running buffer (20×; Life Technologies, cat. no. NP0002), iBlot transfer stacks, nitrocellulose, regular size (Life Technologies, cat. no. IB3010-01), Anti-p38α rabbit primary antibody (Santa Cruz Biotechnology, cat. no. sc-535), Anti-β-actin mouse primary antibody (Santa Cruz Biotechnology, cat. no. sc-69879), Bovine anti-rabbit horseradish peroxidase (HRP)-conjugated secondary antibody (Santa Cruz Biotechnology, cat. no. sc-2374), Goat antimouse HRP-conjugated secondary antibody (Santa Cruz Biotechnology, cat. no. sc-2055), Clarity western enhanced chemiluminescence (ECL) substrate (Bio-Rad, cat. no. 170-5061), AlphaScreen SureFire p38 MAPK α Total (PerkinElmer, cat. no. TGRT38S500), AlphaScreen SureFire ERK 1/2 total (PerkinElmer, cat. no. TGRTES 10K), AlphaScreen IgG detection kit (Protein A; PerkinElmer, cat. no. 6760617M)

Equipment

Veriti 96-well thermal cycler (Life Technologies, cat. no. 4375786), MicroAmp eight-tube strip, 0.2 ml (Life Technologies, cat. no. N8010580), MicroAmp eight-cap strip (Life Technologies, cat. no. N8010535), INCO 108 CO2 incubator (Memmert, Fisher Scientific cat. no. 11574306), Leica DM IL inverted microscope (Leica Microsystems), XCe114 SureLock Midi-Cell (Life Technologies, cat. no. WR0100), iBlot gel transfer device (Life Technologies, cat. no. IB1001EU), PowerPac basic power supply (Bio-Rad, cat. no. 164-5050), Single channel pipettes (Rainin, Pipette-lite L-2XLS, L-20XLS, L-200XLS and L-1000XLS), Pipette tips (Rainin, SS-L10, SS-L250 and SS-L1000), Electronic multichannel pipettes (Sartorius eLINE; eight-channel, cat. nos. 730320 (0.2-10 µl), 730340 (5-120 µl) and 730390 (50-1,200 µl)), CyBi-TipTray 96 25 µl (CyBio, cat. no. OL 3800-25-533-N), Thermowell aluminum sealing tape (Corning, cat. no. 6570), Pipette epTips (epTips, cat. nos. 05-403-39 (0.2-20 µl), 05-403-41 (2-200 µl) and 05-403-68 (50-1,000 µl)), Electronic pipette tips (Optifit Tips, cat. nos. 790010 (0.2-10 µl), 790302 (5-300 µl) and 791200 (50-1, 200 OA Microcentrifuge (Eppendorf, cat. no. 5424 000.215; PCR-tube rotor, cat. no. 5424 708.005), Microcentrifuge tubes (Sarstedt, 1.5 ml cat. no. 72.706; 2 ml cat. no. 72.695.500), ChemiDoc MP system (Bio-Rad, cat. no. 170-8280), Milli-Q system (Millipore), See-saw rocker SSL4 (Stuart, SSL4), Conical tubes (Sarstedt, 15 ml cat. no. 62.554.502; 50 ml cat. no. 62.547.254), Serological pipettes (Sarstedt, 2 ml, cat. no. 86.1252.001; 5 ml, cat. no. 86.1253.001; and 10 ml cat. no. 86.1254.001), Cell culture flasks (BD Falcon; T25, cat. no. 353109; T75, cat. no. 353136; and T175, cat. no. 353112), Costar 12-well culture plate (Corning, cat. no. 3512), Moxi Z automated cell counter (VWR, cat. no. 734-2477), Moxi Z Type S cassettes (VWR, cat. no. 734-2482), TC20 automated cell counter (Bio-Rad, cat. no. 145-0102), Counting slides for TC20 (Bio-Rad, cat. no. 145-0015), Envision 2104 multilabel reader (PerkinElmer, cat. no. 2104-0010), Multidrop 384 reagent dispenser (Thermo Scientific, cat. no. 5840150), Standard tube dispensing cassette (Thermo Scientific, cat. no. 24072670), Multidrop Combi reagent dispenser (Thermo Scientific, cat. no. 5840300), Small tube plastic tip dispensing cassette (Thermo Scientific, cat. no. 24073290), CyBi-Well 96/384-channel simultaneous pipettor (CyBio, cat. no. 3391 3 4112), IKA-Schuttler MTS 4 microplate shaker (IKA), TECHNE TC-PLUS thermal cycler (Bibby Scientific, cat. no. ELITE02), Nunc U-bottom 96-well polypropylene plates, clear (Nunc, cat. no. 267245), Twin.tec PCR 96-well plate, skirted (Eppendorf, cat. no. 0030 128 672), ProxiPlate-384 Plus, white shallow-well microplate (PerkinElmer, cat. no. 6008289), Echo 550 liquid handler (Labcyte), Echo qualified 384-well low dead volume microplate (384LDV; Labcyte, cat. no. LP-0200)

Cell culture medium FBS added to RPMI to a final concentration of 10% (vol/vol) and antibiotic-antimycotic solution to a working concentration of 100 units/ml penicillin, 100 μg/ml streptomycin and 250 ng/ml Fungizone. Supplemented cell culture medium to be stored at 4° C.

The culture medium should be preheated to 37° C. using a water bath before use in cell culture experiments. Fresh 1-glutamine is added before seeding and splitting to a working concentration of 2 mM.

Cells HL-60 cells are used in the example used in the procedure.

PBS 200 ml of PBS buffer can be prepared by dissolving one PBS tablet in 200 ml of ultrapure water. Complete EDTA-free protease inhibitor should be added to the PBS before use.

Reducing loading buffer 800 μl of reducing loading buffer can be prepared by mixing 560 μl of 4× NuPAGE LDS sample buffer with 240 μl of 10× NuPAGE reducing agent before use.

Western blot wash buffer One TBS-Tween tablet can be dissolved in 500 ml of Milli-Q water to obtain TBS with 0.05% (wt/vol) Tween (TBST).

Western blot blocking buffer 2.5 g of nonfat dry milk can be dissolved in 50 ml of TBST to obtain 5% (wt/vol) nonfat milk.

Clarity western ECL substrate kit Equal volumes of Clarity luminol substrate and Clarity peroxide solution can be mixed.

Acceptor bead mix Preparation of the acceptor bead mix is according to the manufacturer's specifications (SureFire kit) by diluting the activation buffer fivefold in reaction buffer. The acceptor beads (from the Protein A IgG detection kit) are then diluted 50-fold in the prepared mix of activation and reaction buffer.

Donor bead mix Donor beads (from the Protein A IgG detection kit) are diluted 20-fold in dilution buffer (from the SureFire kit) immediately before use according to the manufacturer's specifications. The donor beads are light-sensitive, so must be handled in subdued light.

PerkinElmer lysis buffer Dilution of the 5× lysis buffer (from the SureFire kit) fivefold in double-distilled water according to the manufacturer's specifications is carried out.

Methods

Determination of a Melting Curve for an Intracellular Protein Using a Two Antibody Detection Method.

HL60 cells were expanded in cell culture medium to about 2 million cells per ml, where approximately 120 million cells were required to determine four melting curves. 15 ml of the 2 million HL60 cells/ml of suspension were added to four separate T75 flasks. 30 μl of 10 ml DMSO stock solution of AMG-548, SB203580 and ERK 1e were added to individual flasks to a final concentration of 20 μM of each compound. The same volume of DMSO was added to the remaining flask as a control. The cell suspensions were mixed gently by pipetting. The cells were incubated for 1 hour at 37° C. The cell suspension was then collected and cells were transferred to 15 ml conical tubes. Cell numbers were counted and cell viability assessed. The conical tubes were then centrifuged at 300 g for 3 minutes at room temperature to pellet the cells and the culture medium was discarded.

Cell pellets were then resuspended with 15 ml PBS and centrifuged for 3 minutes at 300 g at room temperature. 1 ml of PBS supplemented with protease inhibitors was added to each tube and the pellet resuspended. Each cell suspension was distributed into ten different 0.2 ml PCR tubes with 100 μl of cell suspension in each tube, with each of the ten tubes to be heated at a different temperature.

The PCR tubes were heated at their designated temperature (40-55 and 58-67° C.) for 3 minutes in a Veriti 96 well thermal cycler. Immediately after hating, the tubes were removed and incubated at room temperature for 3 minutes. The samples were then snap-frozen.

Cell lysis was carried out by freeze-thawing the cells twice using liquid nitrogen and a thermal cycler at 25° C. The tubes were vortexed after being thawed and the cell lysates kept on ice after the last thawing. The cell lysates were then centrifuged at 20000 g for 20 minutes at 4° C. to pellet the cell debris. Finally, 90 μl of lysate was then transferred to a new tube for analysis.

Analysis was carried out using the alphascreen format. Each lysate was diluted 15 fold in 1× PerkinElmer lysis buffer (from the AlphaScreen SureFire kit) and the contents mixed carefully. 4 μl of each solution was transferred from the PCR tubes to a separate well of a 384-well ProxiPlate. 5 μl of acceptor beads were added and the plate sealed with a Thermowell plate seal and agitated for 5 minutes at 500 rpm. The plate was then incubated for 2 hours at room temperature. 2 μl of donor beads were then added an the plate sealed and centrifuged at 100 g at room temperature for 10 seconds. The plate was then agitated for 5 minutes at 500 rpm. The plate was incubated at room temperature for at least 2 hours and chemiluminescence read using an Envision plate reader. Data processing software (e.g. GraphPad Prism) was used to evaluate the data.

Analysis was also carried out by Western blotting and use of an anti-p38 IgG rabbit primary antibody, together with a bovine anti-rabbit HRP-conjugated IgG secondary antibody.

Determination of an Isothermal Dose-Response Fingerprint for an Intracellular Protein The procedure is the same as above for generating a melting curve, except that the compound concentration is varied instead of the temperature when heating cells. Thus, in this method, HL-60 cells were expanded in cell culture medium to a cell density of 1-2 million cells/ml using standard cell culture. The cell suspension was collected and transferred to 15 ml conical tubes. The conical tubes were centrifuged at 300 g for 3 minutes at room temperature and the medium discarded. The cell pellet was resuspended in fresh media to provide a cell density of approximately 40 million cells/ml. 15 μl of 4 mM DMSO stock solution of AMG-548, SB203580 and ERK 11e compounds was placed in separate wells of column 1 a 96 U Nunc plate. 100 DMSO was placed in columns 2-12. The stock solutions were serially diluted by transferring 50 from columns 1 to 2, mixing and then by continuing this process one column at a time until column 11, where a final 50 is removed and discarded. Column 12 acted as a control. A second plate was prepared as a backup by splitting the serial dilutions into the second plate. All the serially diluted solutions were diluted 50 fold by adding cell culture media. 5 μl of all diluted compound solutions were then transferred to a Twin.tec PCR plate. 15 μl of the homogenous cell suspension was added to each well of the plate and the plate was incubated for 30 minutes at 37° C. The plate was shaken every 10 minutes.

The PCR plate was then incubated in a thermal cycler (Techne) and heated for 3 minutes at 50° C. The plate was then placed in an aluminium block for 3 minutes to ensure consistent cooling.

Detection was then carried out using the AlphaScreen method. 140 µl of PerkinElmer lysis buffer was added to each well and the cell suspensions were mixed with the buffer. 4 µl of sample was then transferred from the PCR plate to a quadrant of the 384-well ProxiPlate. 5 µl of the acceptor bead mix was added and the plate sealed with Thermowell plate seals. The plate was then agitated for about 5 minutes at 500 rpm. The plate was then further incubated for 2 hours at room temperature. 2 µl of donor bead mix was then added and the plate sealed and centrifuged at 100 g at room temperature for 10 seconds. The plate was then agitated for about 5 minutes at 500 rpm. Subsequently the plate was incubated at room temperature for at least 2 hours. The Luminescence was read using an Envision plate reader and data software (e.g. GraphPad Orism) was used to evaluate the luminescence data.

Analysis was also alternatively carried out by Western blotting and use of an anti-p38 IgG rabbit primary antibody, together with a bovine anti-rabbit HRP-conjugated IgG secondary antibody.

Results

FIG. 12 shows the expected results from melting curve experiments in the absence (controls) and presence of stabilizing ligands for a system based on the protein kinase p38α. The western blots show the presence of the protein at the lower test temperatures followed by its disappearance as the temperature increases FIG. 12A right). An apparent decrease in protein amounts at the lowest temperature can also be seen, due to the so-called hook effect, because of restricted target protein access for the antibody. The relative intensities of the bands were quantified and plotted as a function of temperature to yield the apparent melting curve, (FIG. 12A left). The relative chemiluminescence values measured using an AlphaScreen-based detection protocol was plotted versus temperature to give the same type of apparent melting curve (FIG. 12B). The apparent Tagg values (given as averages±s.d.) for p38α in HL-60 cells and the absence of inhibitors was 48±0.8 and 46.7±0.7° C. for the western blot and AlphaScreen approaches, respectively. A shift of the apparent Tagg value to 54.8±0.6° C. (western blot) and 53.7±0.6° C. (AlphaScreen) for SB203580 and 60.6±1.0° C. (western blot) and 59.2±0.9° C. (AlphaScreen) for AMG-548 showed the consistent response between the detection method of Western blotting and Alphascreen. A lack of a substantial response in the presence of 20 µM of the known ERK1/2 inhibitor ERK 11e was observed.

On the basis of these results, the temperature at which to pursue ITDRFCETSA experiments (i.e. the dose experiments) can be determined. In the present example, using p38α, this was done at 50° C., i.e., at a temperature at which the majority of unliganded protein is denatured and precipitated (FIG. 12).

When performing the ITDRFCETSA experiments, an increased presence of target protein is expected, as the ligand concentration is increased to levels where protein binding saturates (since the experiment is conducted at a temperature where a major portion of the target protein denatures and precipitates unless it is thermally stabilized by the ligand). The increased protein levels were observed on the western blot (FIG. 13A right). The relative intensities were plotted after quantification as a function of ligand concentration to generate the ITDRFCETSA curve in (FIG. 13A left). FIG. 13B shows the corresponding data for the homogeneous assay using AlphaScreen-based detection. The concentrations at which half-maximal thermal stabilization of p38α in HL-60 cells is observed were calculated. In these examples, the outcome was 0.41±0.12 µM (western blot) and 0.26±0.11 µM (AlphaScreen) for SB203580 and 19±7 nM (western blot) and 35±16 nM (AlphaScreen) for AMG-548, whereas ERK 11e did not result in any stabilization within the tested concentration range. Again, excellent consistency is shown between the two tested detection methods.

EXAMPLE 10

High Throughput Screening for Identification of Stabilisers of Intracellular p38α

The procedure is very similar to that described for Example 9 (dose response experiment), although this assay allows the parallel processing of larger numbers of plates simultaneously. This example shows the testing of library compounds at one concentration, but the same procedure can be applied for a dose-response characterisation. This example shows the analysis of 352 different compounds with 16 positive and 16 negative controls.

Methods

HL-60 cells were expanded in cell culture medium to a density of approximately 1.5-2 million cells/ml. The cell suspension was collected and the cells transferred to 15 ml conical tubes. The tubes were then centrifuged at 300 g for 3 mins at room temperature and the media was discarded. The cell pellet was resuspended in media to a cell density of about 30 million cells/ml. Compound source plates were prepared by placing 10 mM DMSO stock solutions of the library compounds in a Labcyte 384 LDV plate. The plates are sealed and stored. The Echo 550 acoustic liquid dispenser was used to place 20 nl of the 10 mM DMSO stock solution in each well of four separate Twin tec PCR plates in columns 1-11. 40 nl of 10 mM DMSO stock solution of SB203580, was added to wells A-D in column 12 as a positive control and 20 nl DMSO was added to welss E-H in column 12 as a negative control. 20 µl of the homogenous cell suspension was added to the plates and the plates were incubated for 30 mins at 37° C. The plates were shaken every 10 mins.

The plates were placed in a thermal cycler and heated for 3 mins at 50° C. and were then removed and placed in an aluminium block for 3 mins at room temperature.

140 µl of 1× PerkinElmer lysis buffer was added to all wells and the wells were mixed. 4 µl of the samples were transferred to quadrant one of the 384-well ProxiPlate. This was done for all 96-well plates. 5 µl of acceptor beads were then added and the plates sealed and agitated for 5 mins at 500 rpm. The plates were then incubated at room temperature for 2 hours. 2 µl of donor beads were then added, the plate sealed and centrifuged for 10 seconds at 100 g at room temperature. The plate was agitated for 5 mins at 500 rpm and then incubated for at least 2 hours. The chemiluminescence was read with a Envision plate reader and evaluated using data processing software as described previously.

Results

The feasibility of applying the homogeneous assay for screen purposes was assessed by testing the homogeneous assay protocol to determine how this responds to the presence of a small set of test compounds taken from a diversity library. To prepare such a test plate, three compounds positioned in wells G06, D02 and E09 were moved and replaced these with 10 mM DMSO solutions of ERK 11e, SB203580 and AMG-548, respectively. In the library, the 12th column in a 96-well plate is for controls. The plate was then tested in the homogeneous AlphaScreen-based CETSA assay at two different concentrations of the library compounds (at 10 and 50 µM, respectively). The results are shown in FIG. 14 as a scatterplot of the observed fold increase of the AlphaScreen signal after normalization on the basis of DMSO-only controls. Both AMG-548 in well E09 and SB203580 in well D02 can be identified as stabilizing hits at both screen concentrations, whereas ERK 11e in position G06 cannot be distinguished from the rest of the inactive compounds. The response for the majority of compounds was very similar to that of DMSO-only controls. At 50 µM, there are also two additional compounds in wells E06 and G08 that appear as weak stabilizers, although they are outside the limit as defined by the average plus three standard deviations of the response for all included compounds (controls excluded). These compounds, called CBK200177 and CBK107148, were also subjected to the ITDRFCETSA procedure, confirming their thermal-stabilizing effect on p38α. Thus the homogeneous assay format can be used in a screen format to identify ligands.

EXAMPLE 11

Using PLA for Membrane Proteins e.g. Integral Membrane Proteins

In order to be able to use CETSA on membrane proteins, the proximity ligation method can be used where two antibodies, targeting different epitopes (or the same epitope, if for example homodimeric proteins are investigated) are used with a proximity reporter assay such as for example alpha lisa or proximity ligation assay. In this example proximity ligation assay was used on intact endothelial cells to verify the presence of—and the heterodimeric nature of VEGFR2 and VEGFR3. Thus, by means of PLA, the presence of natively folded complexes of membrane proteins or single membrane proteins can be visualised.

Materials and Methods

Cells are harvested and fixed in 4% PFA (30 minutes on ice). The PLA protocol from O-link was used by first blocking the slides followed by addition of the antibodies targeting VEGFR2 and VEGFR3 and PLA probed secondary antibodies towards the primary antibodies. The probes are oligonucleotides that are unique for the secondary antibody. Addition of a bridging probe that in the event of proximity between the antibodies and oligonucleotides allows ligation of the oligonucleotides and a rolling circle amplification of the double stranded DNA. The detection of amplified DNA is made by addition of complementary fluorescent probes using a confocal microscope.

Results

The number of heterodimers was visualised as a bright fluorescent signal and counted by image analysis software. The system made it possible to show that addition of certain mammalian endothelial growth factors (called VEGFs) induced heterodimerisation between VEGFR2 and VEGFR3 after treating the cells prior to chemical fixation.

The invention claimed is:

1. A method of determining whether a non-purified sample contains a target protein bound to a ligand of interest comprising the steps of:
   (a) exposing the non-purified sample to a temperature which is capable of causing or enhancing precipitation of the unbound target protein to a greater extent than it is capable of causing or enhancing precipitation of the target protein bound to the ligand; and
   (b) analysing said sample for the presence of soluble or native target protein using two or more affinity reagents capable of binding to said soluble or native target protein with a higher affinity than to an unfolded and/or insoluble form of said target protein.

2. The method of claim 1 wherein at least one of said affinity reagents is an antibody.

3. The method of claim 1 wherein two affinity reagents are used.

4. The method of claim 3 wherein the two affinity reagents are antibodies.

5. The method of claim 1 wherein each affinity reagent is conjugated to a different label and wherein a change in signal from at least one label is generated when said two or more affinity reagents are bound to said soluble or native target protein.

6. The method of claim 5 wherein said different labels are conjugated to or comprised within separate bead populations.

7. The method of claim 1 wherein said soluble target protein is detected by FRET or BRET.

8. The method of claim 1 wherein said method does not comprise a step of separation.

9. The method of claim 1 wherein said target protein is comprised within or on a cell.

10. The method of claim 1 wherein said target protein is a membrane protein.

11. The method of claim 1 wherein said sample is further subjected to conditions capable of causing cell lysis, after step (a).

12. The method of claim 1 wherein said sample is a cell colony, a liquid culture of cells or a patient or animal sample or an histology sample.

13. The method of claim 12 wherein the patient or animal sample is obtained directly from the patient or animal and/or is a tissue sample.

14. The method of claim 13 wherein the tissue sample is blood, serum, plasma or lymph.

15. The method of claim 1 wherein the temperature is equal to or greater than the initial melting temperature of the target protein.

16. The method of claim 1 wherein the non-purified sample is exposed to a series of different temperatures, including a temperature which is equal to or greater than the initial melting temperature of the target protein.

17. The method of claim 1 where the non-purified sample is a section of an histology sample and wherein said sample is exposed to a constant temperature which is greater than the initial melting temperature of the target protein.

* * * * *